(12) United States Patent  (10) Patent No.: US 8,397,731 B1
Perper et al.  (45) Date of Patent: Mar. 19, 2013

(54) ADJUSTABLE, RADIO-TRANSLUCENT CHEST, NECK, AND HEAD SUPPORT ARM ATTACHMENT FOR C-ARM TABLES FOR RADIOSCOPY-GUIDED PROCEDURES

(76) Inventors: Yakov Perper, Valley Stream, NY (US); Sergey Jivetin, High Falls, NY (US); Satoru W. Bauman, Kingston, NY (US)

( * ) Notice: Subject to any disclaimer, the term of this patent is extended or adjusted under 35 U.S.C. 154(b) by 261 days.

(21) Appl. No.: 12/835,735

(22) Filed: Jul. 13, 2010

Related U.S. Application Data

(63) Continuation-in-part of application No. 12/685,414, filed on Jan. 11, 2010.

(60) Provisional application No. 61/144,079, filed on Jan. 12, 2009.

(51) Int. Cl.
*A61G 15/00* (2006.01)
*A61F 5/37* (2006.01)
*A47C 20/00* (2006.01)

(52) U.S. Cl. .............................. 128/845; 128/846; 5/635

(58) Field of Classification Search .......... 128/845–846; 5/635–636, 621–622, 648, 601, 208–209; 602/20, 32; 600/417; 601/23–25, 240–242, 601/244, 237
See application file for complete search history.

(56) References Cited

U.S. PATENT DOCUMENTS

| | | | | |
|---|---|---|---|---|
| 6,435,186 | B1 * | 8/2002 | Klemm | 128/845 |
| 6,488,030 | B1 * | 12/2002 | Wardle et al. | 128/845 |
| 6,662,392 | B2 * | 12/2003 | Heimbrock | 5/621 |
| 8,025,279 | B2 * | 9/2011 | Seber | 269/143 |
| 2007/0007400 | A1 * | 1/2007 | James | 248/125.1 |
| 2008/0034502 | A1 * | 2/2008 | Copeland et al. | 5/621 |

* cited by examiner

*Primary Examiner* — Michael Brown
*Assistant Examiner* — Ophelia A Hawthorne
(74) *Attorney, Agent, or Firm* — O'Connell Law Firm

(57) ABSTRACT

A fluoroscopy chair convertible between a chair configuration for use during fluoroscopic procedures to a support table configuration. The fluoroscopy chair has a seat, a support column supporting the seat, a radiotranslucent chest support retained to an anterior side of the seat, and a back support retained to the posterior side of the seat. The back support is reconfigurable between a first configuration that forms an upstanding surface and a second configuration cooperating with the seat to form a support table. The chest support, which can have multiple, differently contoured support surfaces, can be adjusted vertically and rotated relative to the patient. A support arm attachment for use during fluoroscopic procedures in relation to a support table with a support platform with a base portion, a mechanism for selectively retaining the base portion relative to the platform of the support table, a support arm retained by the base portion, and a chest and neck support retained by the support arm.

17 Claims, 23 Drawing Sheets

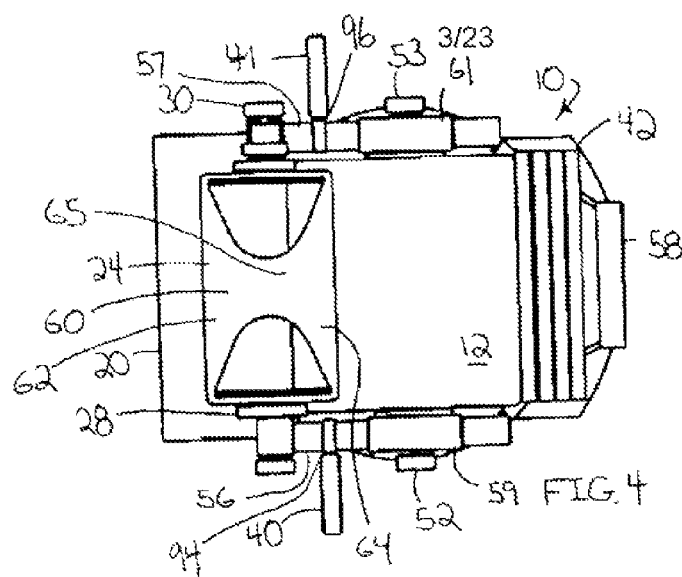
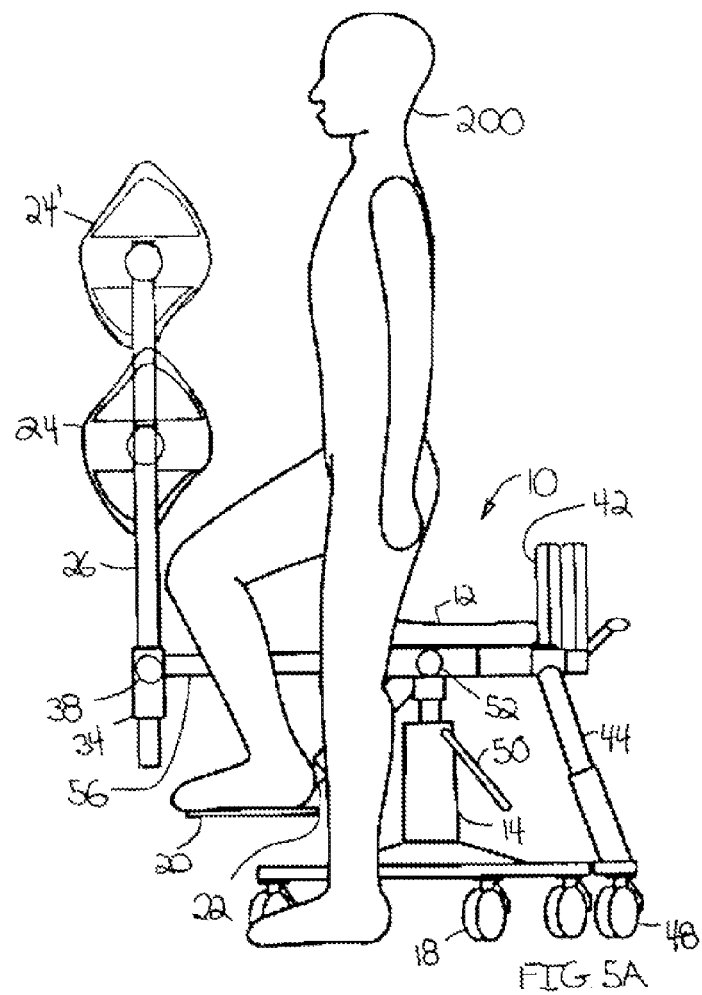

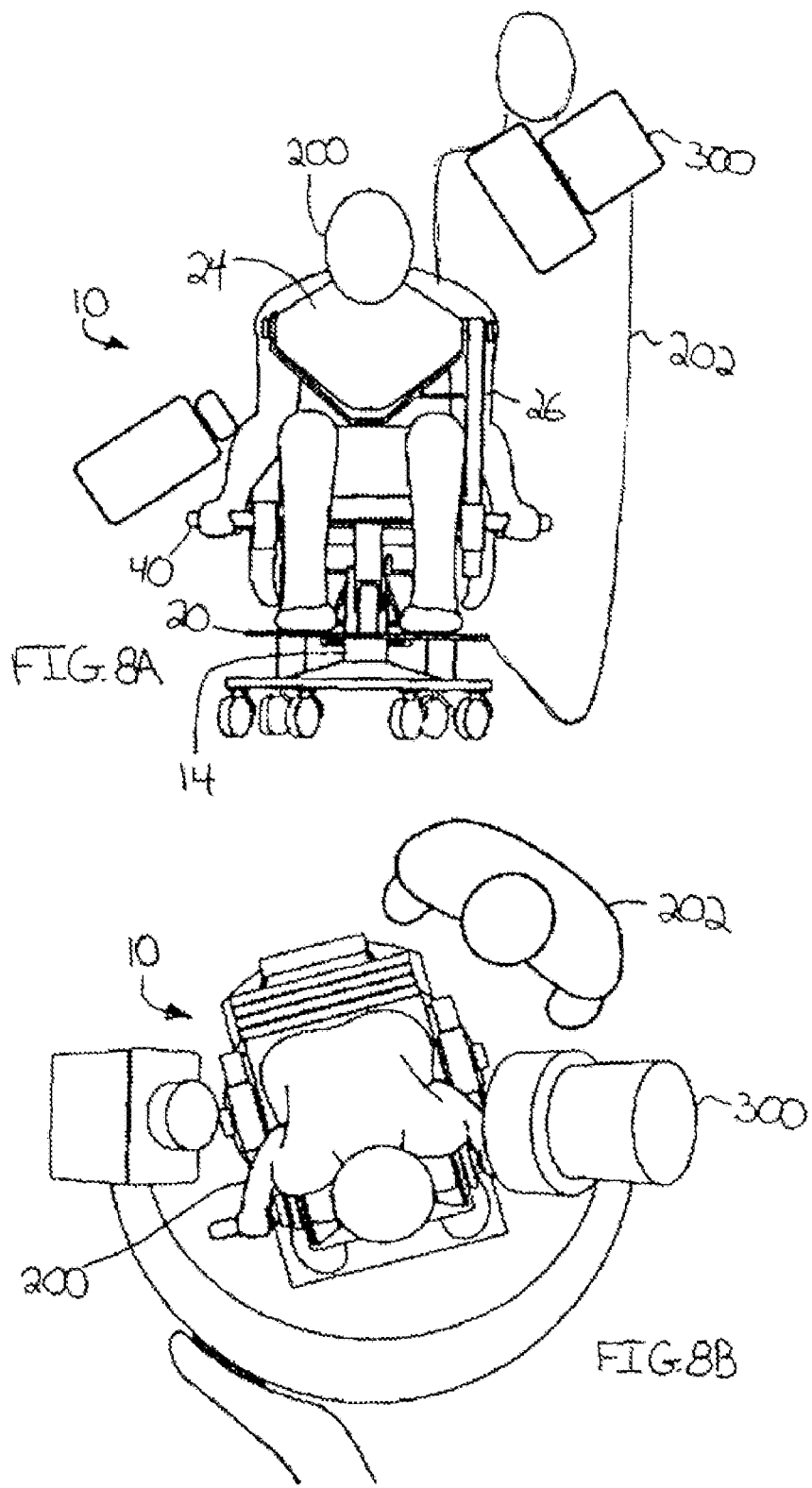

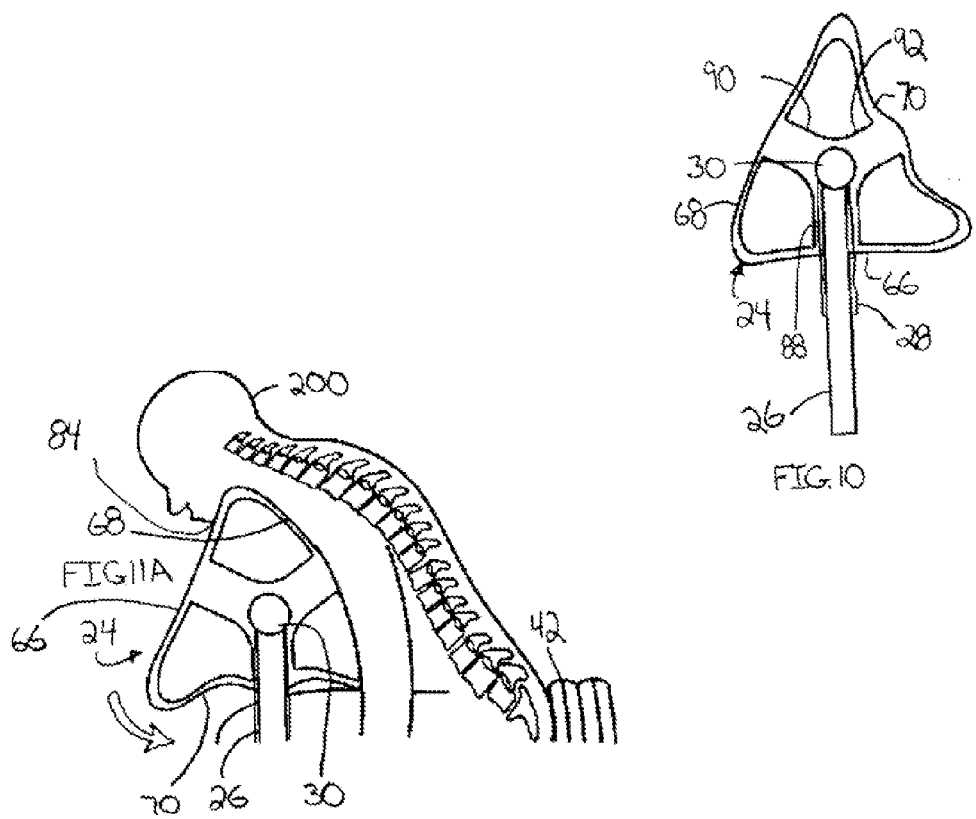
FIG. 10
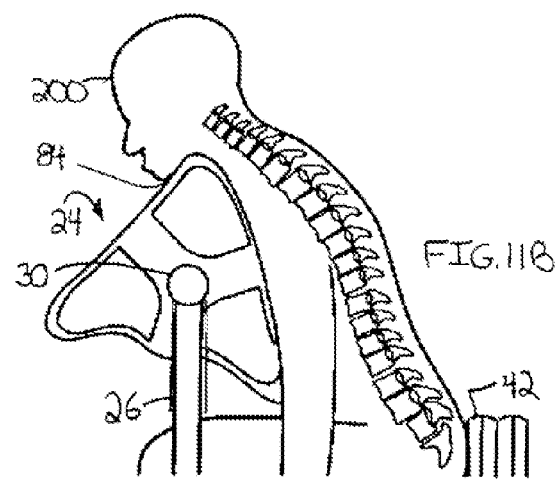
FIG. 11A
FIG. 11B

ADJUSTABLE, RADIO-TRANSLUCENT CHEST, NECK, AND HEAD SUPPORT ARM ATTACHMENT FOR C-ARM TABLES FOR RADIOSCOPY-GUIDED PROCEDURES

This application is a continuation-in-part of U.S. patent application Ser. No. 12/685,414, filed on Jan. 11, 2010, which claims the benefit of Provisional Application No. 61/144,079, filed Jan. 12, 2009.

FIELD OF THE INVENTION

The present invention relates generally to patient support chairs and to support arm attachments for C-arm fluoroscopic procedures. More particularly, disclosed herein is a chair for use during fluoroscopic procedures that provides radiolucent, adjustable chest and lower back supports for interventional pain management procedures that is capable of rapid conversion to a resuscitation table in emergency situations. Also disclosed herein is a support arm attachment for being retained relative to a C-arm table to provide adjustable, radiolucent chest, neck, and head support to a patient while permitting immediate adjustment of the patient to a resuscitation position on the C-arm table.

BACKGROUND OF THE INVENTION

During interventional pain management, drugs are injected into the patient's body to reduce and otherwise manage pain and, in certain cases, to assist in the identification of the source of pain. The most commonly performed procedure to relieve pain is an epidural steroid injection where a powerful cortisone solution is injected directly to the spine to reduce swelling and irritation around a nerve or part of the spinal cord. In a second procedure, referred to as selective nerve root injection, fluoroscopy provides X-ray guidance to enable a drug to be injected directly into a troubled nerve root rather than into the entire spine. In facet joint injection, medication is injected directly into a facet joint, again relying on the aid of fluoroscopic X-ray guidance. In yet another procedure, an injection is made into the sacroiliac joint. Interventional pain management also includes injections of corticosteroids directly into an affected joint or soft tissue space.

Knowing the precise depth and position of the needle is critically important to the effective introduction of the pain management drug and, just as importantly, to avoiding serious complications. Therefore, as noted above, each procedure is simultaneously guided by anterior-posterior, oblique, and lateral fluoroscopy.

Even with fluoroscopic guidance, however, interventional pain procedures at the cervical and thoracic spine present a number of challenges to the pain practitioner. This is often due to the inability to obtain an optimal fluoroscopy view of the lower cervical and thoracic spine. Compromised fluoroscopic viewing can derive from a number of sources, including fluoroscopic obstructions presented by the patient support arrangement and challenges in patient positioning. Both are largely beyond the control of the practitioner under the present state of the art.

Under current medical practices, common patient positioning options include the prone, supine, and recumbent positions, the left and right lateral decubitus positions on a horizontal table, and the sitting position in a chair or on a table. The recumbent and lateral decubitus positions offer patients comfort but can create difficulties with fluoroscopic visualization of the spine. For example, when a patient is in the prone position, the lower cervical segments are sometimes difficult to visualize in the lateral view due to the patient's shoulder obstructing the X-ray beam.

Pain practitioners use several techniques seeking to improve the visualization of the lateral view of the lower cervical region. They sometimes ask the patient to simulate a swimming position with one shoulder up and the other down or to pull both shoulders down. In other cases, practitioners place a pillow under the patient's shoulders to improve the cervical curvature. Practitioners also sometimes increase the X-ray beam for better X-ray penetration. Although these measures work for some patients, they do not work for everyone and often do not fully resolve the issue. For example, some patients cannot obtain these positions. In other cases, the positions do not improve visualization. Furthermore, such measures are time consuming and increase the radiational exposure for the patient and the staff.

It is also difficult to visualize the interlaminar spaces in the thoracic spine because of the significant caudal angulation of the spinal processes. To obtain a better view, interventionalists often put a pillow under the chest to increase thoracic curvature and thus to open the intralaminar spaces. Alternatively, the procedure can be done in the sitting or lateral decubitus position to provide better flexion of the thoracic spine.

The seated position is known to be advantageous in that it offers better visualization of the lower cervical and the thoracic spine and enables improved access for fluoroscopy guided procedures. Gravity pushing the patient's shoulders down facilitates visualization of the lower cervical segments. Additionally, it is easier to extend or bend the neck in the sitting position compared to the lying position. The seated position also gives more freedom to permit flexibility of the thoracic spine thus easing the fluoroscopy of the thoracic intralaminar spaces and facilitating access to the thoracic epidural spaces.

For the lumbar spine, the sitting position can be preferred for many reasons, one being a patient's inability to tolerate the recumbent position, such as due to severe low back pain. For patients with severe breathing conditions, such as COPD, CHF, and asthma, and wheelchair dependent or morbidly obese patients, the sitting position may be the only solution for performing spinal procedures at any level: lumbar, thoracic, or cervical.

In the absence of dedicated equipment, doctors commonly use a number of techniques to modify the existing medical and non-medical apparatuses for this procedure. For example, the patient can be seated in a massage chair, a regular patient chair with a step stool under the feet, a regular chair with the chin on the fluorotable, and other ad hoc positioning arrangements. While they can at times be simple to administer, these methods create health and safety problems for the patient and the pain practitioner. For example, such positioning arrangements lack a radiolucent chest and chin support whereby fluoroscopic viewing can be obstructed. Furthermore, the practitioner is often unable to obtain optimal fluoroscopic views in each of the anterior-posterior, oblique, and lateral planes.

Positioning methods of the prior art also often require lengthy and complicated emergency supine patient repositioning. However, in an emergency situation, such as a vasovagal reaction, anaphylactic shock, or disrythmias, every second before emergency assistance can be provided is critical. As the present inventor has appreciated, quick and safe supine repositioning can be life saving.

With a knowledge of the state of the art as summarized above, certain of the present inventors created a fluoroscopy chair that is readily convertible to a resuscitation table as is disclosed in their application Ser. No. 12/685,414, which is incorporated herein by reference. The chair is advantageous for its safer and more comfortable positioning for the patient and for its more effective and convenient fluoroscopy of the upper, middle, and lower spine. Moreover, the chair allows the patient to remain in a forward-leaning and relaxed seated position when fluoroscopy of the cervical, thoracic, or lumbar spine is taken during interventional procedures. Perhaps most importantly, the chair allows quick supine repositioning of the patient. For these reasons, the disclosed chair is believed to represent a significant advance in the art of patient supports.

While the fluoroscopy chair is believed to be effective and advantageous for its intended purpose, the inventors have further appreciated that there may be circumstances where a dedicated fluoroscopy chair as disclosed may be impractical or even impossible. A practitioner, particularly one already be possessed of a fluoroscopy table, may have concerns about adding a further piece of equipment. The practitioner may have concerns as to the space required for the additional equipment. Indeed, there may simply not be room for a separate item of equipment even where the need for the same is clear. There may be equally critical concerns regarding the cost of acquiring new equipment. Therefore, although a practitioner may be highly desirous of obtaining the advantages of the invention, he or she may be hesitant to bring the dedicated fluoroscopy chair into the practitioner's facility.

Accordingly, while the need for the inventors' previously devised fluoroscopy chair is apparent, there is also a need for a support arm attachment that can be employed relative to a pre-existing article of equipment, such as a C-arm table, to provide adjustable, radio-lucent chest, neck, and head support during radioscopy-guided procedures.

SUMMARY OF THE INVENTION

With an appreciation for the needs of patients and the challenges in interventional pain management and fluoroscopy positioning deriving therefrom, the present inventors set forth with the fundamental object of providing a fluoroscopy support arrangement that can provide comfortable yet effective support and positioning assistance to patients during fluoroscopy and interventional pain management procedures.

A more particular object of the invention is to provide a fluoroscopy chair that facilitates fluoroscopic viewing during interventional pain management.

An underlying object of embodiments of the invention is to provide a fluoroscopy chair with radiolucent support members to permit enhanced, unobstructed fluoroscopic viewing.

A further underlying object of embodiments of the invention is to provide a fluoroscopy chair capable of providing adjustable support for efficient and comfortable positioning during interventional procedures.

Still another object of certain embodiments of the invention is to provide a fluoroscopy chair that can be readily converted to a resuscitation table to accommodate emergency situations.

A further object of the invention is to provide a fluoroscopy chair that minimizes the need for C-arm repositioning.

Yet another object of the invention is to provide a fluoroscopy chair that facilitates effective interventional pain management with minimized exposure to radiation.

In alternative embodiments, a fundamental object of the invention is to provide a support arm that can be selectively attached to a pre-existing article of equipment, such as a C-arm table, to provide adjustable, radio-lucent chest, neck, and head support during radioscopy-guided procedures.

A related object of such embodiments of the invention is to provide a support arm attachment that avoids the need for a dedicated item of equipment by providing added functionality to a pre-existing item of equipment.

Another object of such embodiments of the invention is to provide a support arm attachment that can be adjusted to a storage position during periods of non-use.

These and in all likelihood further objects and advantages of the present invention will become obvious not only to one who reviews the present specification and drawings but also to those who have an opportunity to make use of an embodiment of the fluoroscopy chair and support arm attachment disclosed herein. Although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In carrying forth these objects, a basic embodiment of the invention essentially comprises a fluoroscopy chair that is convertible between a chair configuration for use during fluoroscopic procedures and a support table configuration for allowing, among other things, emergency intervention procedures. The fluoroscopy chair is founded on a seat with an anterior side, a posterior side, a left side, and a right side. An extendable and retractable support column acts as a means for supporting the seat. A chest support is retained to the anterior side of the seat and has a chest support surface for supporting a chest of a patient seated on the seat. To permit unobstructed fluoroscopy, a body portion and in fact the entire chest support can be radiotranslucent, such as by being molded as a shell from a carbon fiber composite. A back support, which is retained to the posterior side of the seat, is reconfigurable between a first configuration that forms an upstanding surface relative to the seat to provide positioning support to the patient and a second configuration wherein the back support cooperates with the seat to form a support table.

The chest support can be adjustable in position in relation to the seat, such as by being adjustable in height and anteriorly and posteriorly in relation to the seat. Furthermore, the chest support can have multiple chest support surfaces, and a means can be provided for selectively orienting the chest support to dispose a chest support surface from among the multiple chest support surfaces oriented to provide primary support to the chest of the patient seated on the seat. That means can be carried forth by a rotatable engagement between the chest support and a support arm to permit the chest support to be rotated about a lateral pivot axis relative to the seat. Additionally or alternatively, the means for selectively orienting the chest support can take the form of a means, such as left and right support sleeves for selectively receiving the support arm, for retaining the chest support in 180-degree opposite orientations about a vertical axis.

Where multiple support surfaces are provided, they can have different surface contours, such as by being inwardly bowed and outwardly bowed. A diamond-shaped chest support can have four support surfaces, two bowed outwardly and two bowed inwardly. A triangular-shaped chest support can have three support surfaces. One can be bowed outwardly, one bowed inwardly, and one with a reverse-curved support surface.

A chin support can be retained relative to the chest support. In certain embodiments with multiple support surfaces, for example, the chin support can comprise a depression formed adjacent to an edge of one of the support surfaces so that a chin of the patient can be disposed in the chin support while the chest of the patient rests an adjacent support surface.

Left and right handles can be retained outboard of the seat. The handles can be adjustable in height in relation to the seat and potentially adjustable anteriorly and posteriorly in relation to the seat.

Under certain constructions of the invention, the back support can take the form of a plurality of pivotally coupled panels that can be retained by first and second frameworks that are slidable in relation to the seat to be extendable and retractable relative to the posterior side of the seat. At least a proximal panel of the plurality of panels can be disposed in an upstanding orientation when the back support is in the first configuration, and the plurality of panels can lie flat and in general alignment with the seat when the back support is in the second configuration.

In other embodiments, the back support can comprise a framework pivotally coupled adjacent to the posterior side of the seat. The framework can have a first framework portion that projects above the seat and a second framework portion that projects below the seat when the back support is in the first configuration. The framework can be slidable relative to the seat to a raised position with the first framework portion extended distally above the seat and an abbreviated portion of the second framework portion that extended below the seat. With that, the framework can be pivoted to the second configuration with the first framework portion in general alignment with the seat to form a support table and with the abbreviated portion of the second framework portion below the seat.

One will appreciate that the foregoing discussion broadly outlines the more important goals and features of the invention to enable a better understanding of the detailed description that follows and to instill a better appreciation of the inventors' contribution to the art. Before any particular embodiment or aspect thereof is explained in detail, it must be made clear that the following details of construction and illustrations of inventive concepts are mere examples of the many possible manifestations of the invention.

BRIEF DESCRIPTION OF THE DRAWINGS

The invention may be more completely understood with reference to the accompanying drawings, in which:

FIG. 4 is a top plan view of the fluoroscopy chair of FIG. 1;

FIG. 5A is a view in side elevation of an initial entry of a patient into a fluoroscopy chair as disclosed herein with the chair adjusted to facilitate entry of the patient;

FIGS. 8A through 8D are views in front elevation, top plan, side elevation, and top plan respectively of a patient, fluoroscopy chair, and C-arm apparatus in varied relative positions;

FIG. 10 is a view in side elevation of an alternative chest support pursuant to the instant invention;

FIGS. 11A and 11B are views in side elevation of a patient supported by a fluoroscopy chair as disclosed herein in first and second positions;

DETAILED DESCRIPTION OF PREFERRED EMBODIMENTS

Figure 1:
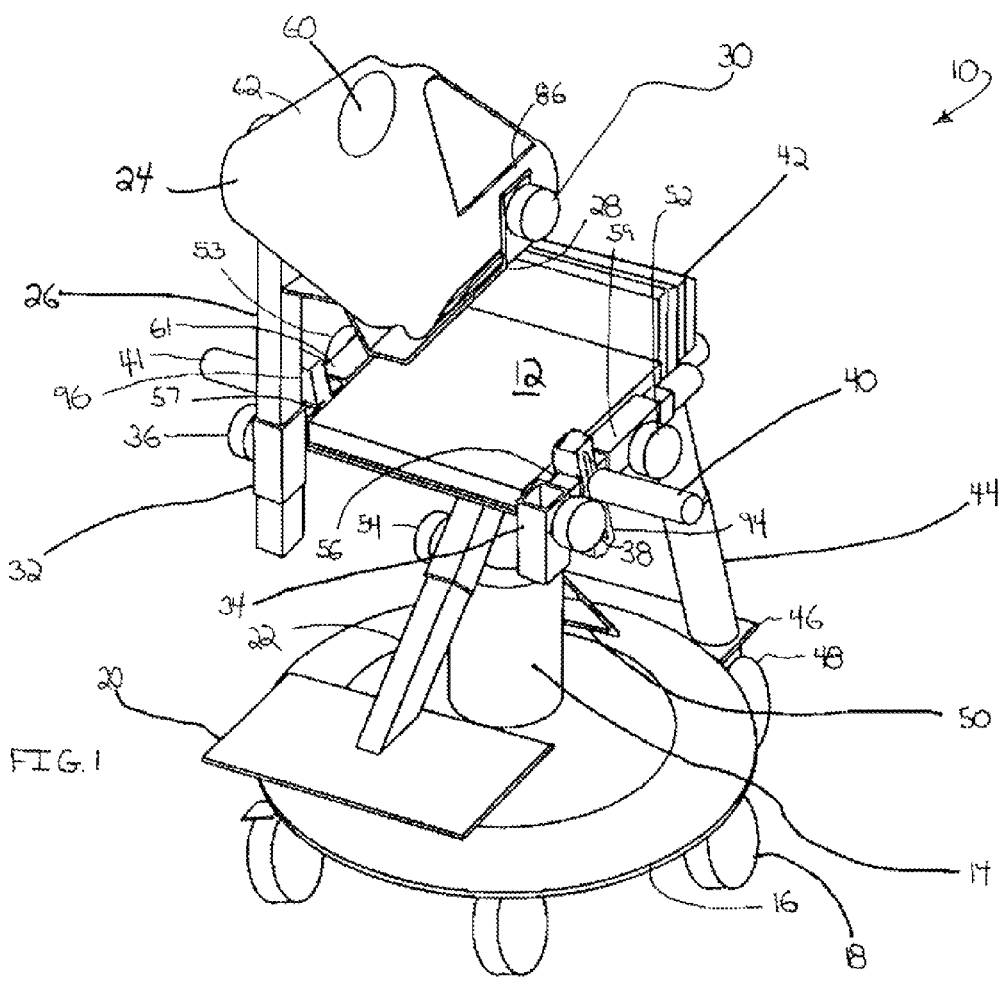
FIG. 1 is a perspective view of a fluoroscopy chair according to the present invention.
Figure 2:
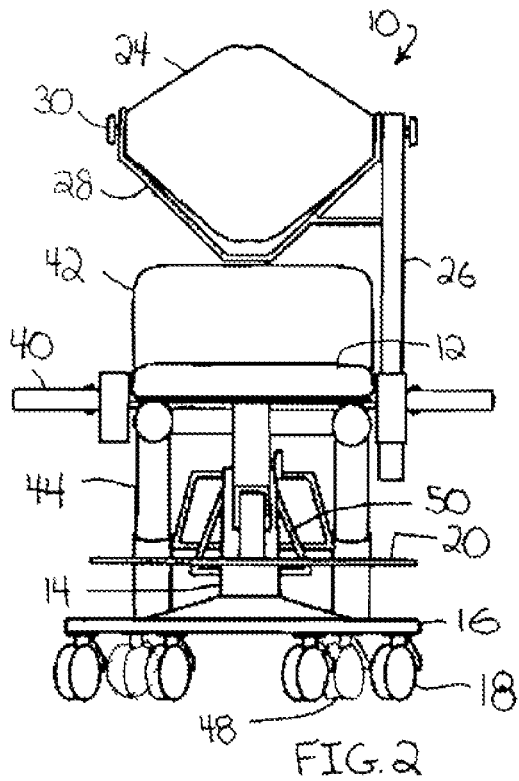
FIG. 2 is a view in front elevation of the fluoroscopy chair of FIG. 1.
Figure 3:
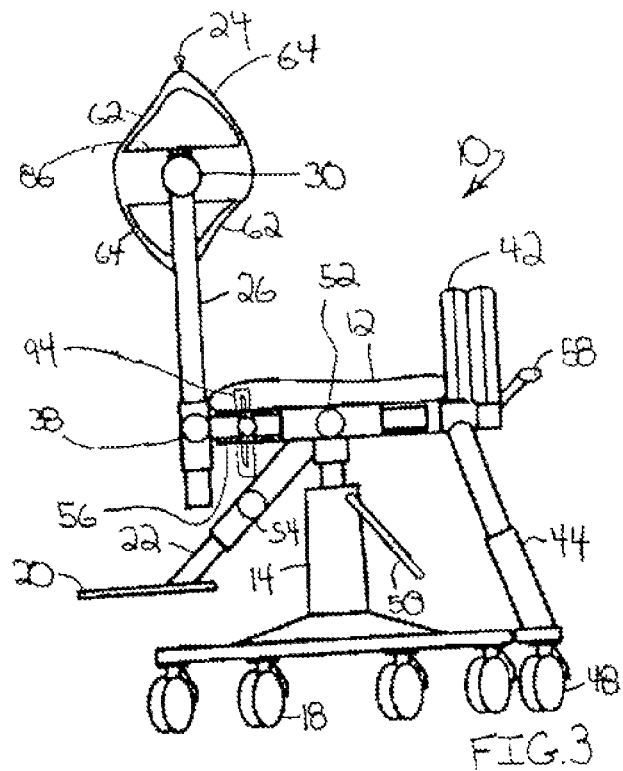
FIG. 3 is a view in side elevation of the fluoroscopy chair of FIG. 1.

As is the case with many inventions, the fluoroscopy chair and support arm attachment disclosed herein can pursue a variety of embodiments within the scope of the invention. However, to ensure that one skilled in the art will be able to understand and, in appropriate cases, practice the invention, certain preferred embodiments of the broader invention revealed herein are described below and shown in the accompanying drawing figures.

An embodiment of a fluoroscopy chair pursuant to the invention is indicated generally at 10 in FIGS. 1 through 4. There, the fluoroscopy chair 10 is founded on a seat 12, which can be flat or contoured, cushioned or solid. A support column 14 has a lower end supported by a base 16 and an upper end that retains the seat 12. The upper end of the support column 14 can be centrally disposed relative to the seat 12 and can permit a relative rotation between the seat 12 and the base 16.

The support column 14 can be extendable and retractable, such as by incorporating or comprising a hydraulic or pneumatic piston arrangement, a threaded coupling, or any other effective means. A means for controlling the extension and retraction of the support column 14, which in this exemplary embodiment comprises a foot lever 50 for actuating the fluidic piston arrangement, can permit an adjustment of the height of the seat 12. The base 16 is in turn supported by a plurality of casters 48 for permitting transportation and repositioning of the fluoroscopy chair 10. The casters 48 can be selectively locked against rotation to fix the fluoroscopy chair 10 in a given location and orientation against inadvertent movement.

A footrest 20 is supported relative to the seat 12 by a support arm 22. The support arm 22 can be selectively extendable and retractable, such as by being formed of first and second sleeves in cooperation with a locking knob 54. The engagement between the locking knob 54 and the support arm 22 can be a clamping arrangement, a mechanical engagement, or any other arrangement for selectively permitting extension and retraction of the support arm 22. In the depicted embodiment, the footrest 20 comprises a single flat panel. It will be appreciated, however, that individual foot supports or other foot support configurations could be provided within the scope of the invention.

A chest support 24 is retained relative to the seat 12 by a support arm 26, which in this embodiment is vertically disposed. The support arm 26 and thus the chest support 24 can be raised and lowered relative to the seat 12. In this embodiment, that raising and lowering is enabled by a slidable reception of the support arm 26 selectively in either a right retaining sleeve 32 or a left retaining sleeve 34 in combination with a locking knob 36 or 38. Again, the locking knobs 36 and 38 can be operative by clamping, mechanical engagement, or any other effective method.

The position of the chest support 24 can additionally be adjusted forwardly and rearwardly into and out of proximity with the seat 12. With this, the position of the chest support 24 can be adjusted to accommodate different patients, to facilitate different fluoroscopic and other procedures as discussed further hereinbelow, and to permit convenient entry and exit relative to the fluoroscopy chair 10. The forward and rearward movement of the chest support 24 could be enabled through a number of different mechanisms. In the current embodiment, the retaining sleeves 32 and 34 are retained by support arms 56 and 57 that are extendably and retractably retained by sleeves 59 and 61 that are fixed to communicate alongside the left and right sides of the seat 12. The support arms 56 and 57, and thus the support arm 26 and the retained chest support 24, can be locked against this longitudinal movement by lock knobs 52 and 53 respectively.

Figure 5B:
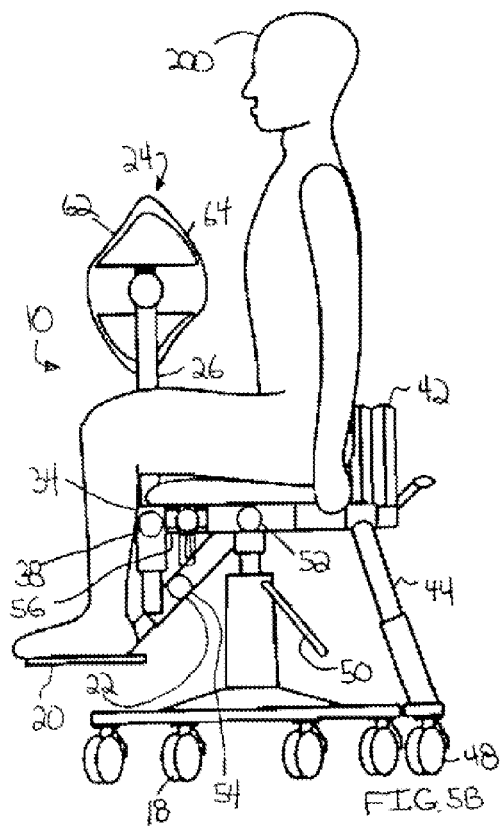
FIG. 5B is a view in side elevation of the patient in the fluoroscopy chair with the chair in a usage configuration.
Figure 5C:
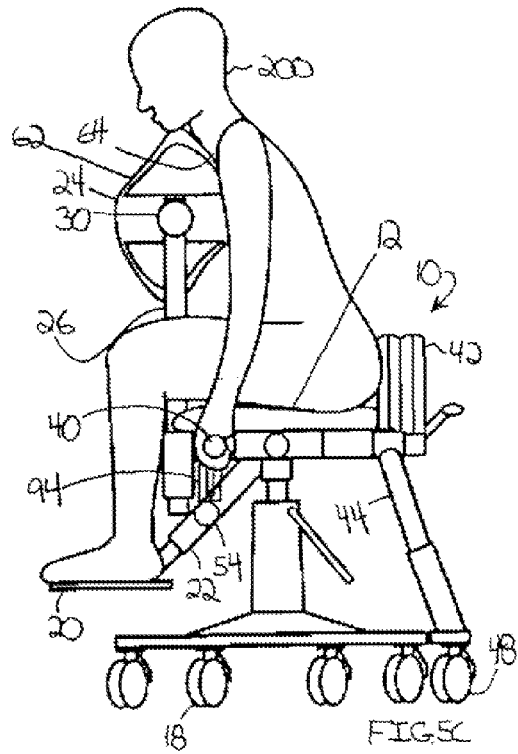
FIG. 5C is a view in side elevation of the patient in the fluoroscopy chair positioned for a fluoroscopy procedure.

Handles 40 and 41 project outboard from the left and right support arms 56 and 57 for being gripped by the patient 200 as shown, for example, in FIG. 5C. The handles 40 and 41 additionally permit control over the movement of the support arms 56 and 57 and thus the chest support 24 through the support arm 26. The handles 40 and 41 can be moved forward and rearward together with or separately from the support arms 56 and 57. Furthermore, by use of vertically disposed, slotted retaining bars 94 and 96, the handles 40 and 41 can be adjusted vertically. Under this construction, the adjustable handles 40 and 41 enhance the comfort of the patient and permit an adjustment of the disposition of the patient's body and shoulders in particular. For example, by lowering the handles 40 and 41, the patient's shoulders will tend to be pulled out of the X-ray beam during lateral fluoroscopic viewing of the lower cervical region.

Figure 9:
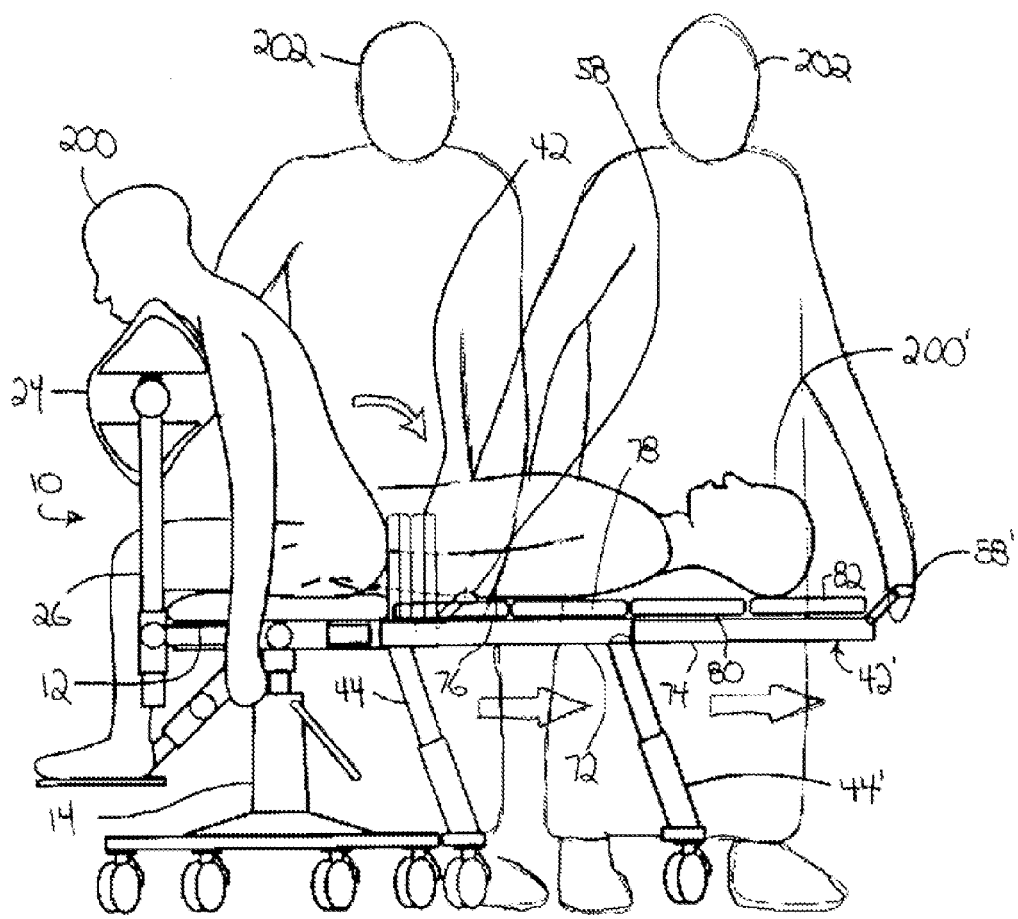
FIG. 9 is a view in side elevation of a fluoroscopy chair according to the invention configured to support a patient during fluoroscopy and reconfigured to a horizontal resuscitation table to accommodate an emergency situation.
Figure 12:
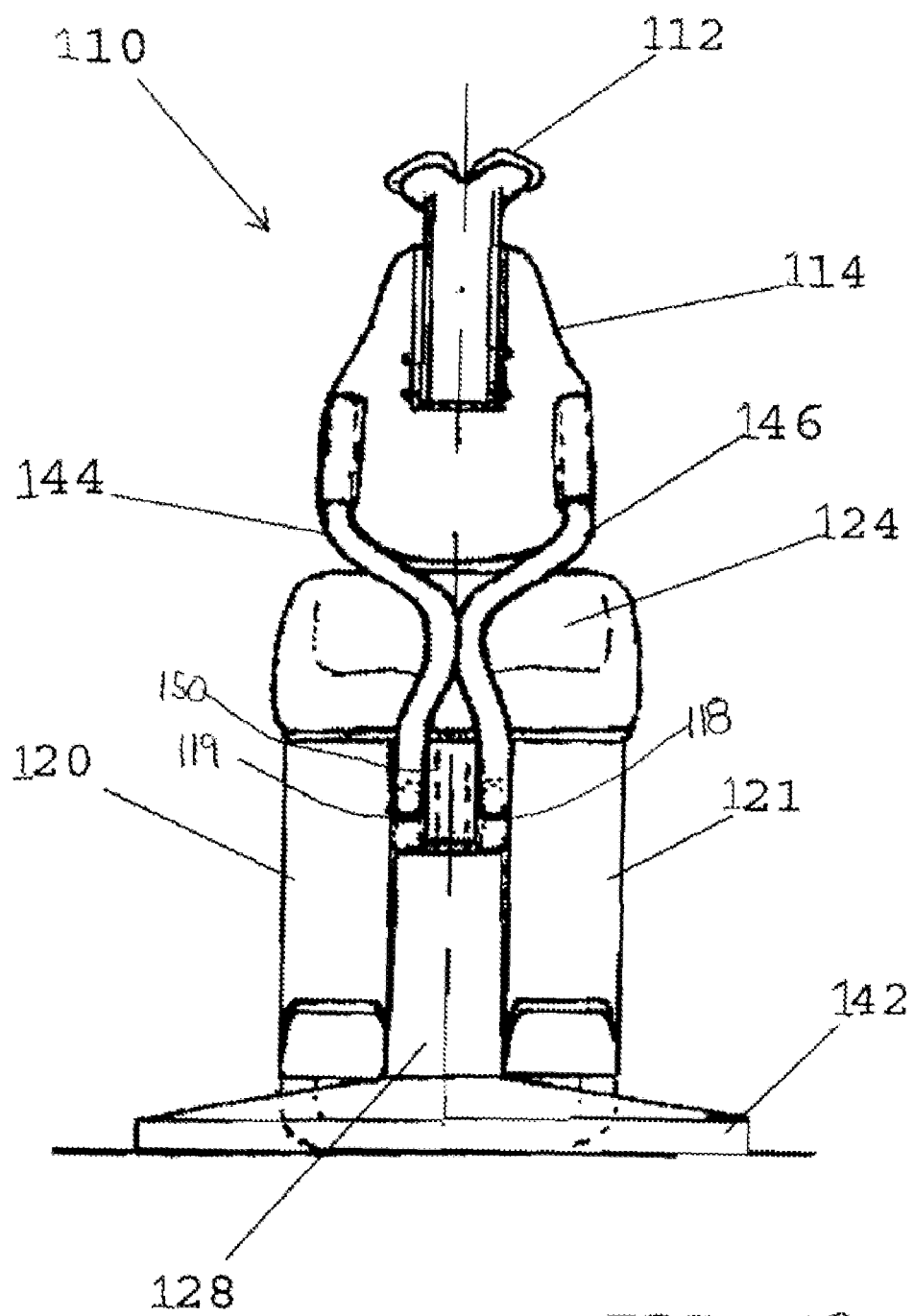
FIG. 12 is a view in front elevation of an alternative fluoroscopy chair pursuant to the invention.

An emergency back support 42 is reconfigurable between the retracted configuration depicted in FIGS. 1 through 4 and the emergency recumbent position shown in FIG. 9. When in a retracted configuration, the back support 42 comprises an upstanding surface generally orthogonal to the seat 12 and provides positioning support to the patient's posterior and lower back. When adjusted to the emergency recumbent position, the back support 42 cooperates with the seat 12 to form a resuscitation table to permit the patient to be repositioned, such as to a recumbent or decubitus position, for emergency assistance or an interventional pain management procedure.

As best perceived by reference to FIG. 9, the back support 42 in the depicted embodiment is formed by first, second, third, and fourth support panels 76, 78, 80, and 82 that are pivotally coupled to one another along lateral pivot axes. When the back support 42 is in the retracted configuration, the support panels 76, 78, 80, and 82 are disposed generally vertically, parallel to one another, and substantially perpendicular to the seat 12. When the back support 42 is in an extended configuration as in FIG. 9, the support panels 76, 78, 80, and 82 achieve a configuration generally coplanar with one another and with the seat 12 thereby forming a table, which in this example is generally horizontal.

The support panels 76, 78, 80, and 82 are supported by proximal and distal support frameworks 72 and 74. The proximal framework 72 is slidably retained by the seat 12, and the distal framework 74 is slidably retained by the proximal framework 72. With this, a practitioner 202 can grasp a handle 58 that is fixed to the distal framework 74 to carry out an extension and retraction of the proximal and distal frameworks 72 and 74 and thus an adjustment of the overall configuration of the back support 42.

By the slidable retention of the proximal framework 72 by the seat 12, the back support 42 is effectively supported at a proximal end thereof by the support column 14 through the seat 12. Additional support is provided for the back support 42 and a patient 200 by back support columns 44. The back support columns 44, which in this example are angled away from the support column 14 for added stability and to accommodate the base 16, have upper ends fixed to the distal end of the proximal framework and lower ends fixed to a support platform 46. The support platform 46 is in turn supported by a plurality of casters 48 that facilitate the extension and retraction of the back support 42. Again, the casters 48 can be selectively locked against rotation to prevent inadvertent movement of the back support columns 44 and the back support 42 in general.

Under this arrangement, the fluoroscopy chair 10 can readily be converted from its chair configuration to a horizontal support table configuration merely by an extension of the proximal and distal frameworks 72 and 74, such as by pulling on the handle 58. The fluoroscopy chair 10, advantageous for its fluoroscopy positioning benefits as summarized herein, can thus be reconfigured to act as a horizontal resuscitation table to accommodate emergency situations. Where other fluoroscopy methods and arrangements have required lengthy, complicated, and potentially dangerous emergency supine patient repositioning, the fluoroscopy chair 10 of the present invention permits a patient 200 simply to be lain back to the position indicated at 200' in FIG. 9 once the back support 42 has been extended to the position indicated at 42' by moving the handle from the position indicated at 58 to the position indicated at 58'. The practitioner can simply move position if necessary from the position indicated at 202 to the position indicated at 202', and safe support will be provided by the support column 14 and the back support columns, which move from the position indicated at 44 to the position indicated at 44' with the distal end of the proximal framework 72. This quick and safe supine repositioning can be life saving in emergency situations, such as vasovagal reactions, anaphylactic shock, and disrythmias, that can arise during interventional pain management procedures.

The chest support 24 is rotatably supported to pivot about a laterally disposed pivot axis, which may be considered an x-axis, by a generally V-shaped support bracket 28 that pivotally retains the chest support 24 at its left and right sides. A lock knob 30 can selectively lock the chest support 24 against rotation in a desired angular position, such as by frictional or mechanical engagement or a combination thereof.

In the current manifestation of the invention, the height, orientation, and longitudinal position of the chest support 24 can be adjusted manually as described and shown herein. Similarly, the height and orientation of the seat 12 and the orientation and location of the fluoroscopy chair 10 itself can be manually adjusted. It will be appreciated, however, that it would be well within the scope of the invention except as it might be expressly limited for electronic, powered control to be provided over some or all of the adjustments.

As in the present embodiment, the chest support 24 can have multiple laterally disposed surfaces for selectively facing a patient 200. The surfaces can have different contours. A rotation of the chest support 24 about its pivot axis can thus cause different surface shapes to be presented to the patient 200. Alternatively, the support arm 26 can be repositioned to the other support sleeve 32 of 34 to turn the chest support 24 by 180 degrees about the vertical or z-axis. In the depicted fluoroscopy chair 10, the chest support 24 is generally diamond shaped with four sides. There are two inwardly bowed surfaces 62 and two outwardly bowed surfaces 64. So configured, the chest support 24 can be employed to good advantage in cervical region interventional pain management procedures.

A chin depression 60, in this case comprising an indentation formed directly within the body of the chest support 24, is disposed adjacent to the edge of each of the inwardly bowed surfaces 62 of the chest support 24. A chin depression 65, also comprising an indentation formed directly within the body of the chest support 24, is disposed adjacent to the edge of each of the outwardly bowed surfaces 64 of the chest support 24. With the provision of the chin depressions 60 and 65, a patient 200 can be positioned with his or her chest against a surface 62 or 64 and his or her chin received into the chin depression 65 or 60 of the adjacent surface 64 or 62. The chin depressions 60 and 65 thus assist with patient positioning while improving patient comfort.

The chest support 24 in this preferred embodiment is formed from radiotranslucent material to produce a chest support 24 that is radiotranslucent. With this, unobstructed, in situ fluoroscopy of the chest, spine, and other body portions of the patient 200 can readily be obtained. A number of methods for creating a radiotranslucent chest support 24 could be devised within the scope of the invention except as it might be expressly limited. In one contemplated construction, the chest support 24 is formed from as a radiotranslucent shell of carbon fiber resin composite. The shell is molded to have the inwardly bowed and outwardly bowed surfaces 62 and 64 disposed with a diamond-shaped cross section. The chest support 24 has open sides. A cross bar 86 bridges across each of the open sides for rotatably engaging and being retained by the support bracket 28. The chin depressions 60 and 65 are formed as by molding directly in the surfaces 62 and 64. Although perhaps less preferred, the chest support 24 could alternatively be formed from radiotranslucent foam or another radiotranslucent material.

Under this arrangement, a patient 200 can be positioned in the fluoroscopy chair 10 as shown in the sequential depictions of FIGS. 5A through 5C where the patient 200 is ultimately positioned for fluoroscopic and interventional pain management procedures in the cervical region. To facilitate the entry of the patient 200 into the chair 10, the chest support 24 can be raised and moved forwardly by sliding the support arm 26 upwardly in the retaining sleeve 32 or 34 and sliding the support arm 56 or 57 outwardly relative to the sleeve 59 or 61. The patient 200 can then sit on the seat 12 and place his or her feet atop the footrest 20. By actuation of the foot lever 50, the height of the seat 12 can be adjusted to suit the patient 200 and the procedure at hand. The position of the footrest 20 can be adjusted by an adjustment of the effective length of the support arm 22 by operation of the locking knob 54. The handles 40 and 41 can be adjusted vertically and along a longitudinal axis to the comfort of the patient 200 and to facilitate the procedure. Still further, the orientation of the seat 12, the chest support 24, the back support 42, and the remaining components retained by the seat 12 together with the seated patient 200 can be adjusted relative to the base 16 and the support surface by a rotation of the seat 12 relative to the base 16. Similarly, the orientation and location of the overall fluoroscopy chair 10 and the patient 200 can be adjusted by use of the casters 18 and 48.

With the patient 200 seated, the chest support 24 can be moved to a desired height by a selective sliding and locking of the support arm 26 relative to the sleeve 32 or 34 and then to a desired longitudinal distance away from the patient 200 by a sliding of the support arm 56 or 57 toward the patient 200 within the sleeve 59 or 61. If desired for proper patient positioning, the surface 62 or 64 of the chest support 24 facing the patient 200 can be adjusted either by rotating the chest support 24 about its pivot axis or by moving the support arm 26 from one sleeve 32 or 34 to the other sleeve 34 or 32. The patient 200 can then lean his or her chest against the facing support surface 62 or 64. With his or her chest against the support surface 62 or 64, the patient can rest his or her chin in the chin depression 65 or 60. By gripping the handles 40 and 41, the shoulders of the patient 200 can be selectively lowered and otherwise manipulated to provide optimal fluoroscopy.

Figure 6:
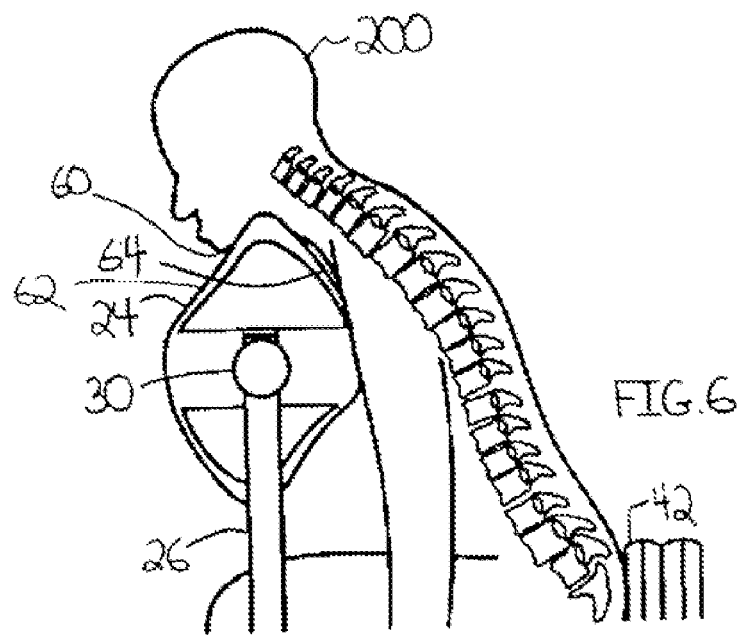
FIG. 6 is a partially sectioned view in side elevation of a patient in the fluoroscopy chair alternatively positioned for a fluoroscopy procedure.
Figure 7A:
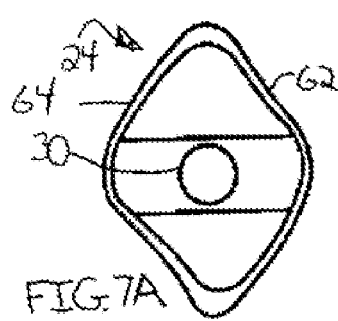
FIGS. 7A and 7B are views in side elevation of a chest support in first and second orientations respectively.
Figure 7B:
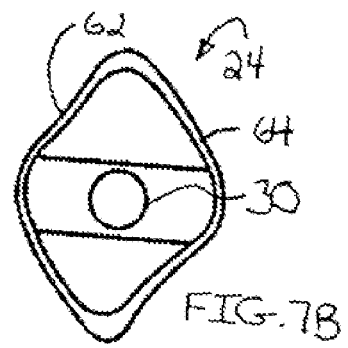
Figure 8C:
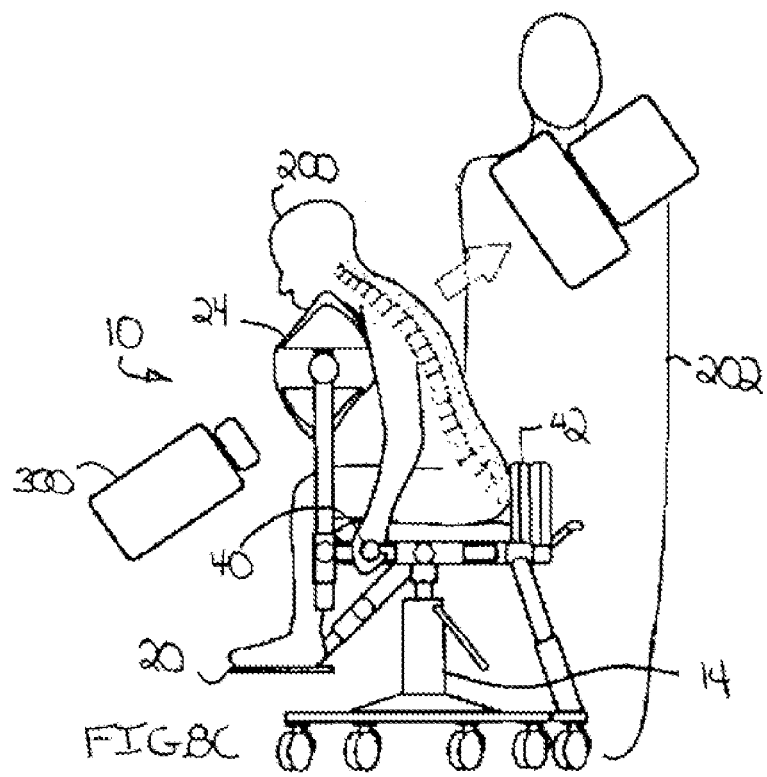
Figure 8D:
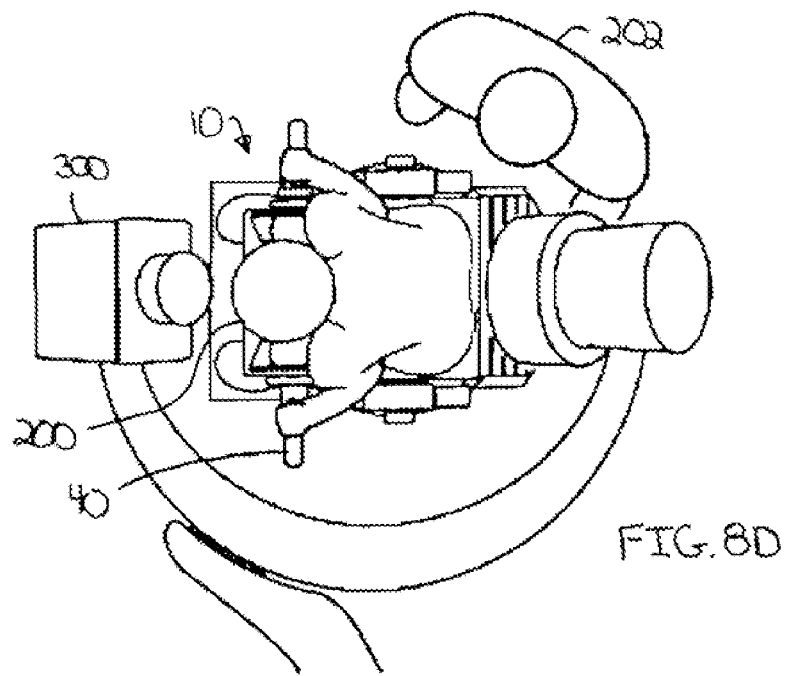

As shown in FIG. 6, the patient's leaning against the outwardly bowed support surface 64 of what can be referred to as the cervical chest support 24 with his chin resting in the chin depression 60 on the inwardly bowed support surface 62 will produce an expansion of the epidural spaces in the patient's cervical region. With this, cervical pain interventional management procedures can be rendered safer and more efficient and convenient for the patient 200 and the practitioner. By a rotation of the chest support 24 or by a movement of the support arm 26 to the other sleeve 32 or 34, the inwardly bowed support surface 62 can be presented for supporting the chest of the patient 200. With that, the patient's spine will be adjusted in its disposition as might be preferred, for example, in an alternative procedure, with a different patient 200, or by a given practitioner.

It will be appreciated that further adjustment of the patient's position may be desirable, such as to extend or bend the spine further or to reduce the spine's extension or to bring the spine to a straighter disposition. Advantageously, the rotatable nature of the chest support 24 can be exploited to induce such further adjustments. For example, where further extension is desired, the chest support 24 can be rotated away from the patient 200. The chest support 24 can be rotated toward the patient 200 where less extension is appropriate.

Once made aware of the present disclosure, one skilled in the art will appreciate that chest supports 24 pursuant to the invention could have fewer, more, and differently shaped sides depending on, among other things, the patient, the procedure, and the preferences of the practitioner. One alternative chest support 24, which is shown apart in FIG. 10 and then in use in FIGS. 11A and 11B, is adapted for use in thoracic region interventional pain management procedures. The thoracic chest support 24 is three-sided with a first, inwardly bowed support surface 66, a second, outwardly bowed support surface 68, and a third, reverse-curve support surface 70, each designed to induce a patient's spine to achieve a differing configuration. The thoracic chest support 24 is again formed as a shell of radiotranslucent material, such as a carbon fiber composite. The chest support 24 establishes a triangular shell with sides that are open except for first, second, and third spokes 88, 90, and 92 that provide structural rigidity to the chest support 24 and permit it to engage and be retained by the support bracket 28 in a rotatable relationship.

Again, the surface 66, 68, or 70 that faces the patient 200 can be selected by a rotation of the chest support 24 about the lateral or x-axis established with the support bracket 28 or by changing the support arm 26 between the left and right sleeves 32 and 34 to enable the optimal positioning of the patient's spine to be achieved. The thoracic chest support 24 can thus produce an expansion of the epidural spaces in the patient's thoracic region as depicted in FIGS. 11A and 11B. By a selective rotation of the chest support 24, a practitioner can further increase or decrease the expansion of epidural spaces in the patient 200 for easing needle penetration and otherwise facilitating the pain management procedure. In FIG. 11A, for example, the chest support 24 is rotated away from the patient 200 by a given degree to cause the epidural spaces to be increasingly opened. In FIG. 11B, however, the chest support 24 is rotated toward the patient 200 in comparison to FIG. 11A whereby the epidural spaces of the patient 200 are only moderately expanded.

As shown in FIGS. 8A through 8D, the fluoroscopy chair 10 can be used to great advantage in conjunction with a C-arm fluoroscopic imaging system 300. Without needing to reposition the C-arm 300, fluoroscopic images in the oblique position as in FIGS. 8A and 8B and the anterior-posterior position as in FIGS. 8C and 8D can be obtained simply by rotating the fluoroscopy chair 10. In each view, the radiolucent chest support 24 permits full, unobstructed fluoroscopy. The experienced practitioner will appreciate that the anterior-posterior, oblique, and lateral plane views obtainable by use of the fluoroscopy chair 10 have been typically difficult or impossible under the positioning methods and arrangements of the prior art.

As noted, different fluoroscopic views can be obtained by rotating the fluoroscopy chair 10 only while leaving the C-arm 300 stationary. However, the C-arm 300 can additionally or alternatively be moved in relation to the fluoroscopy chair 10 as necessary, and the fluoroscopy chair 10 can be adjusted while in a given orientation for optimal positioning of the patient 200. With this, fluoroscopy during interventional pain management can be carried out with a high degree of efficiency and improved accuracy. The time consuming and potentially uncomfortable requirements to move the patient 200 between support apparatuses or between alternative ad hoc arrangements is obviated as is the increased potential for error and adverse repercussions deriving therefrom. Fluoroscopic views can be obtained unobstructed by radio-opaque components at any possible C-arm position while the patient's head, neck, and chest are stably supported by the radiolucent chest support 24.

Figure 13:
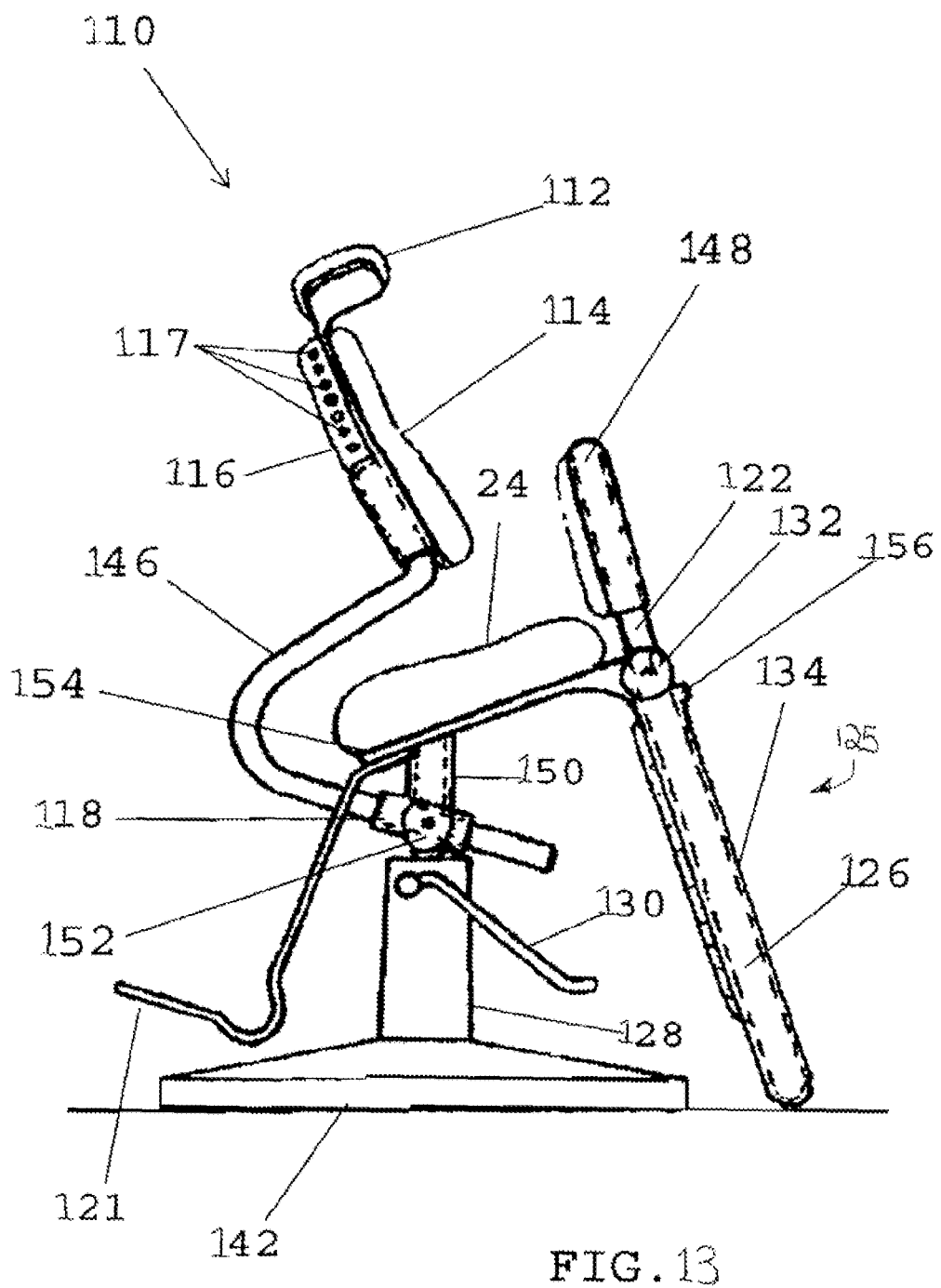
FIG. 13 is a view in side elevation of the fluoroscopy chair of FIG. 12.
Figure 14:
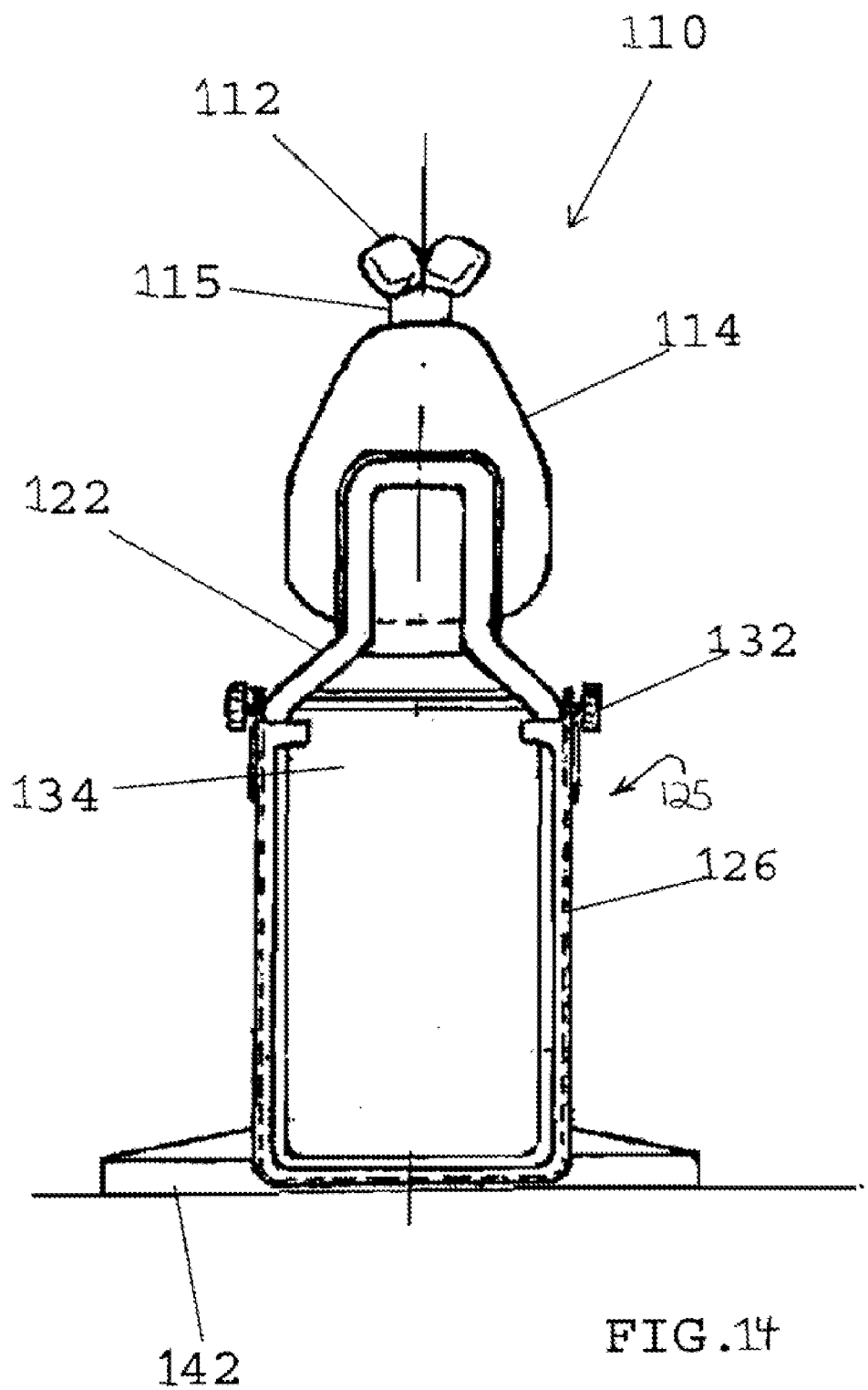
FIG. 14 is a view in rear elevation of the fluoroscopy chair of FIG. 12.

An alternative embodiment of the present invention for a fluoroscopy chair is indicated generally at 110 in FIGS. 12 through 17B. The fluoroscopy chair 110 is founded on a chair base 142 that supports a central column 128. As shown in FIG. 13, a height adjustment foot lever 130 is pivotally coupled to the central column 128 for enabling an extension and retraction of a cylinder 150 relative to the central support column 128 thereby establishing an extendable and retractable piston arrangement. Under this arrangement, the components coupled to move with the cylinder 150 and the seat 124 can be selectively raised and lowered by use of the foot lever 130 as described hereinbelow.

Figure 15:
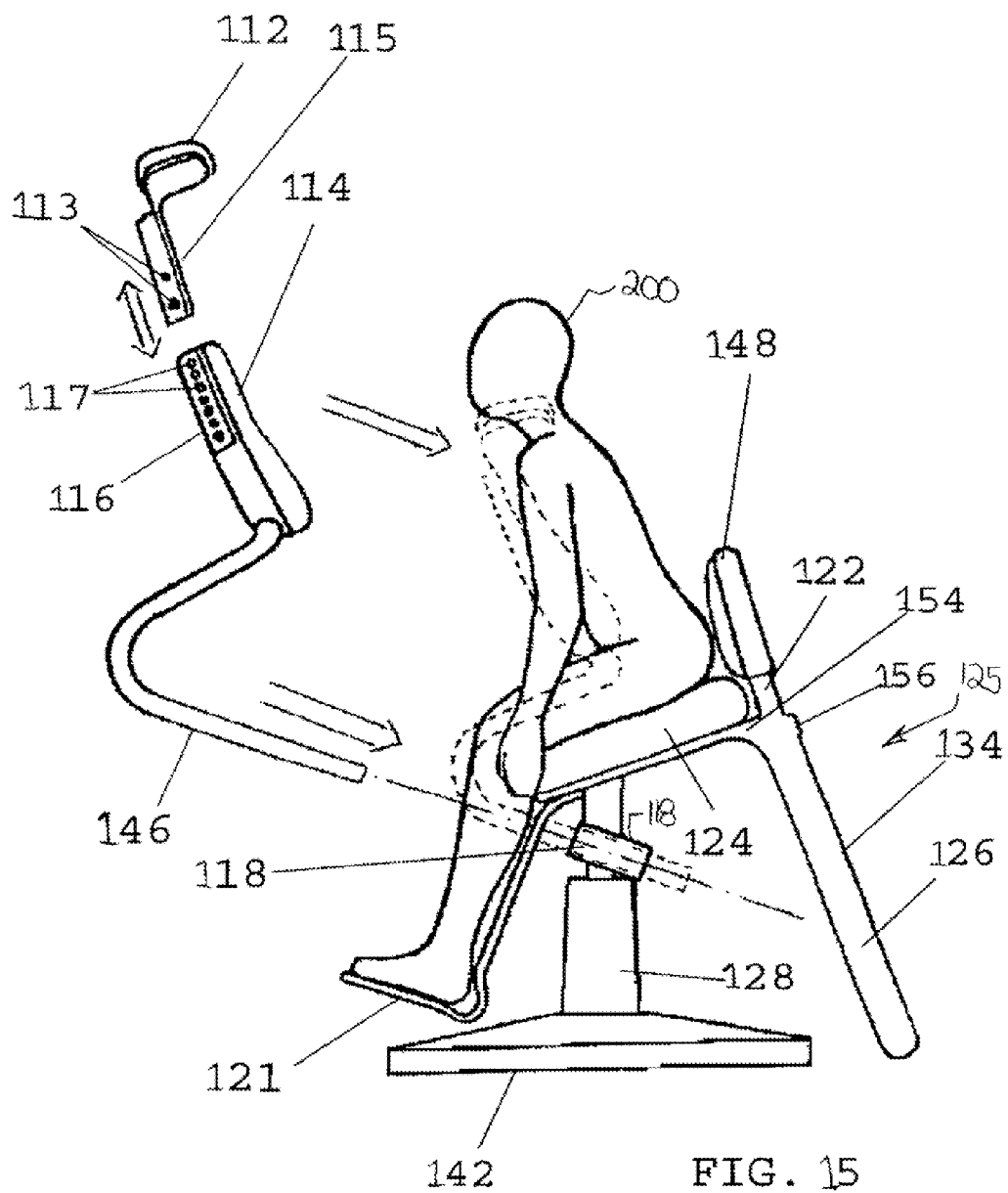
FIG. 15 is a view in side elevation of a patient being positioned in the fluoroscopy chair of FIG. 12.

Left and right chest bar support sleeves 118 and 119 are fixed to opposing sides of the cylinder 150. The sleeves 118 and 119 matingly receive left and right ergonomically shaped support bars 146 and 144. The left and right support bars 146 and 144 have proximal ends received into the sleeves 118 and 119, body portions bowed inwardly toward one another, and distal portions that widen away from one another and then retain a chest support 114. As shown in FIG. 15, the support bars 144 and 146 have a profile with a generally straight chest support portion, a central portion angled anteriorly, and then a reverse curve to a proximal portion angled posteriorly. Support bar locking knobs 152 can be employed to fix the support bars 144 and 146 in place relative to the sleeves 118 and 119. Again, the locking knobs 152 can comprise any suitable locking mechanism, whether a clamping arrangement, a mechanical engagement, or any other effective arrangement.

The chest support 114 and the bars 144 and 146 cooperate to retain an ergonomically contoured chin support 112 that can be selectively raised and lowered based on the size and comfort of the patient, the procedure to be performed, and the goals of the practitioner. In this embodiment, the chin support 112 is fixed to a base member 115 that has first and second compressible buttons 113 disposed therealong. The chest support 114 has a channel 116 with a plurality of apertures 117 disposed therealong. With this, a pressing of the compressible buttons 113 permits a sliding engagement of the base member 115 and the retained chin support 112 relative to the channel 116 and the chest support 114. The chin support 112 can be fixed at a given height by permitting the buttons 113 to engage aligned apertures 117 in the channel 116.

The support bars 144 and 146 are preferably formed form a radiolucent, tubular material or combination of materials exhibiting sufficient strength and rigidity to support even large patients. Again, the radiotranslucent material could be carbon fiber composite or any other suitably strong material. Similarly, the chest support 114 and the chin support 112 are crafted from radiotranslucent material or a combination of radiolucent materials. With this, unobstructed fluoroscopic viewing is permitted even while a patient is supported by the chin and chest supports 112 and 114.

A seat framework 154 is retained at the top of the cylinder 150. In the depicted example, the seat framework 154 is fixed at a given slope, but it will be appreciated that the seat framework 154 could be disposed horizontally or in some other orientation or configuration. A seat cushion 124, which can also be radiolucent, is retained by the seat framework 154 for the comfort of the patient. Left and right leg and foot supports 120 and 121 are fixed to and extend from the seat framework 154. In the depicted embodiment, the leg and foot supports 120 and 121 are generally L-shaped for providing comfortable support to a patient's lower legs and feet.

A back support assembly 125 is pivotally and slidably coupled to a posterior end of the seat framework 154. When the fluoroscopy chair 10 is in a normal chair usage orientation for fluoroscopy, the back support assembly 125 has a first framework portion 122 that projects above the seat framework 154 and the seat cushion 124 in a generally orthogonal disposition as shown, for example, in FIGS. 13 and 15. With this, the first framework portion 122 comprises an upstanding surface relative to the seat cushion 124 when in a normal usage configuration to provide positioning support to a patient. The back support assembly 125 additionally has a second framework portion 126 that projects below the seat framework 154 when the fluoroscopy chair 110 is in a normal seat usage configuration. A locking knob 132 can be employed to lock the back support assembly 125 at a given angle relative to the seat framework 154.

The first and second framework portions 122 and 126 can be radiotranslucent. Furthermore, the first framework portion 122 retains a radiotranslucent cushion 148, and the second framework portion is encased in a radiotranslucent, padded sheath 134.

A patient 200 can thus be situated for fluoroscopy using the fluoroscopy chair 110 as is suggested by FIG. 15. With the chair 110 configured for normal usage, the chest support bars 144 and 146 can be removed from the sleeves 118 and 119 thereby also removing the chin and chest supports 112 and 114. The patient 200 can then be positioned seated on the seat cushion 124 with his or her lower back adjacent to the cushion 148 of the first framework portion 122. Then, the proximal ends of the chest support bars 144 and 146 can be inserted into the sleeves 118 and 119 and adjusted therein until the chest support 114 achieves a location suitable to the patient 200, the practitioner, and the procedure. Then, the height of the chin support 112 can be adjusted as necessary.

Figure 16:
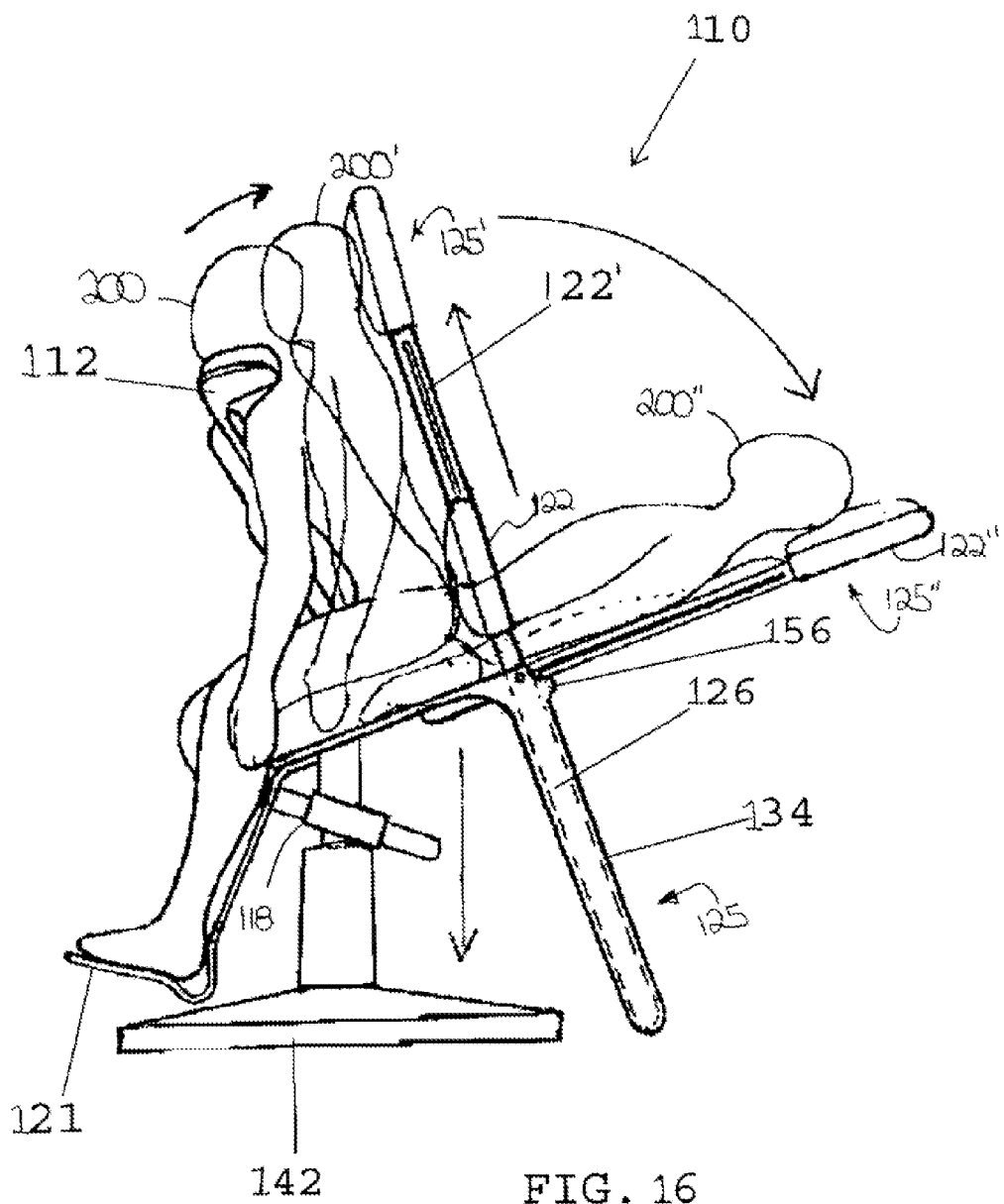
FIG. 16 is a view in side elevation of the fluoroscopy chair of FIG. 12 configured to support a patient during fluoroscopy and reconfigured to a resuscitation table to accommodate an emergency situation.

In an emergency situation, the fluoroscopy chair 110 can be readily reconfigured from its chair configuration to a resuscitation table as is shown in FIG. 16. To achieve that reconfiguration, the first framework portion can first be slid upwardly from the position indicated at 122 to the raised position indicated at 122' until a stop protuberance 156 reaches the seat framework 154 or another dedicated stopping obstruction. The patient can be assisted in moving from the resting position indicated at 200 to a position 200' against the first framework portion 122'. With the back support assembly 125' so configured, only an abbreviated portion of the second framework portion 126 will continue to project below the seat framework 154. Then, the back support assembly 125' can be pivoted relative to the seat framework 154 until the abbreviated protruding portion of the second framework portion 126 contacts the seat framework 154. Further pivoting will be prevented, and the first framework portion and the back support assembly achieve the emergency resuscitation table configuration indicated at 122" and 125" and the patient is supported at the position indicated at 200" ready to receive emergency assistance.

Figure 17A:
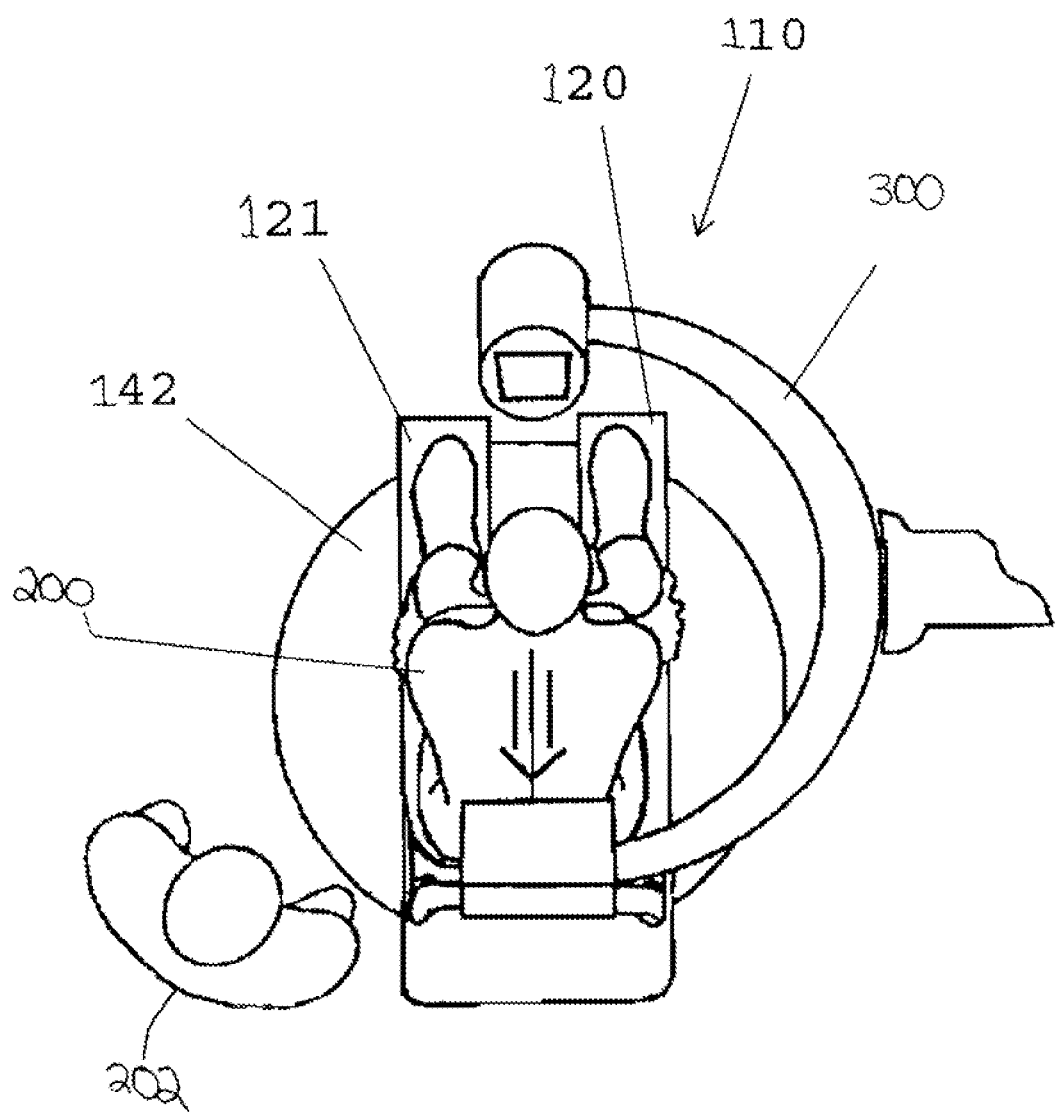
FIG. 17A is a top plan view of the fluoroscopy chair of FIG. 12 with a patient positioned for anterior-posterior fluoroscopic viewing.
Figure 17B:
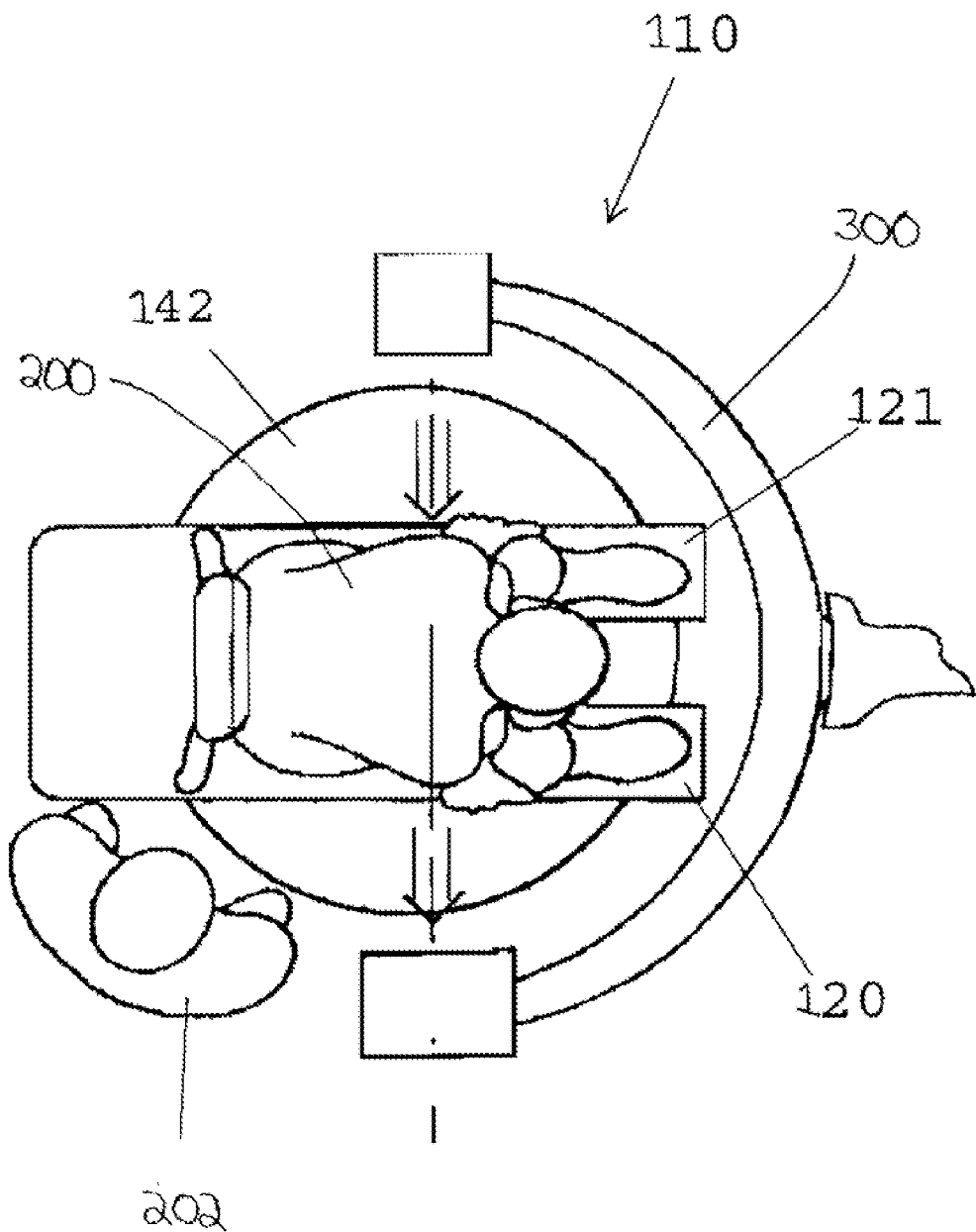
FIG. 17B is a top plan view of the fluoroscopy chair of FIG. 12 with a patient positioned for lateral fluoroscopic viewing.

Turning to FIGS. 17A and 17B, the fluoroscopy chair 110 is shown employed in relation to a C-arm 300 for fluoroscopic imaging. Since the chair 110 can be rotated about the vertical or z-axis, a patient 200 can be safely and conveniently rotated relative to the C-arm 300, which can be retained in a stationary disposition. This rotation of the chair 110 prevents the practitioner 300 from having to reposition the patient 200 and minimizes the need for adjustment of the C-arm 300. Under certain constructions, a rotation lock-and-release mechanism can be installed into the base 142 for ensuring that a desired orientation of the chair 110 is maintained.

Figure 18:
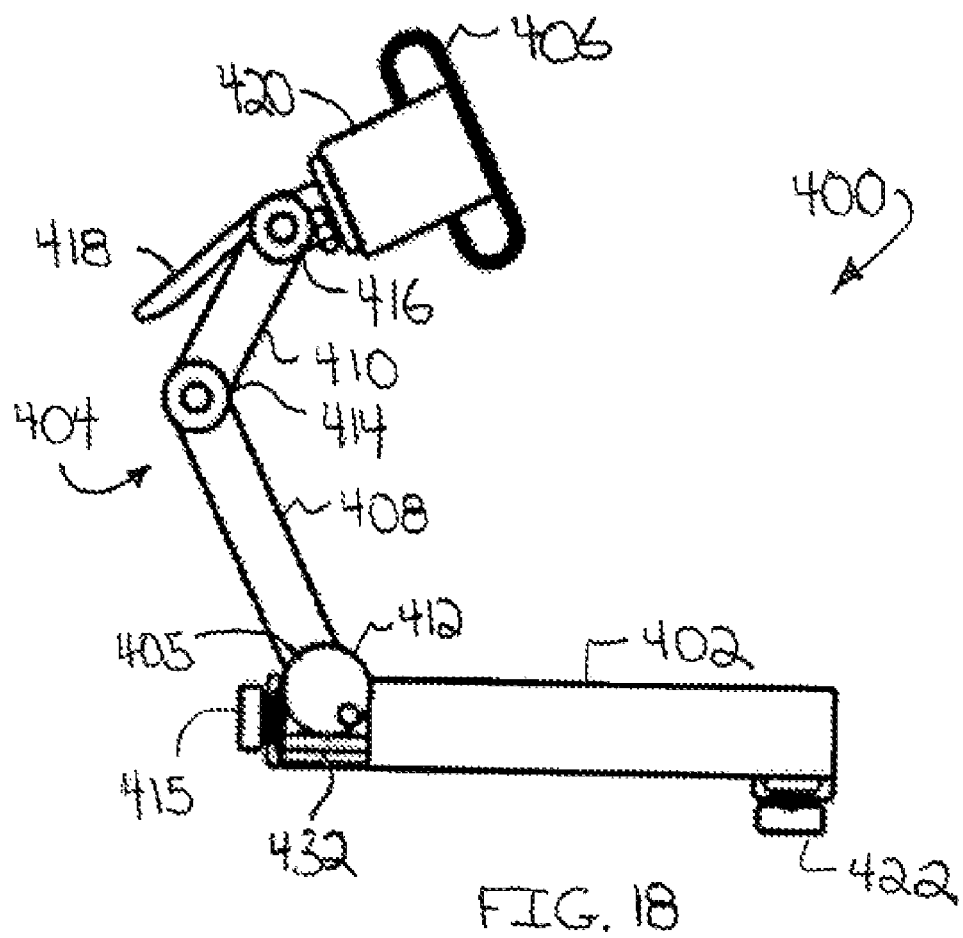
FIG. 18 is a view in side elevation of an adjustable radiotranslucent chest, neck and head support arm attachment for C-arm tables pursuant to the present invention.
Figure 19:
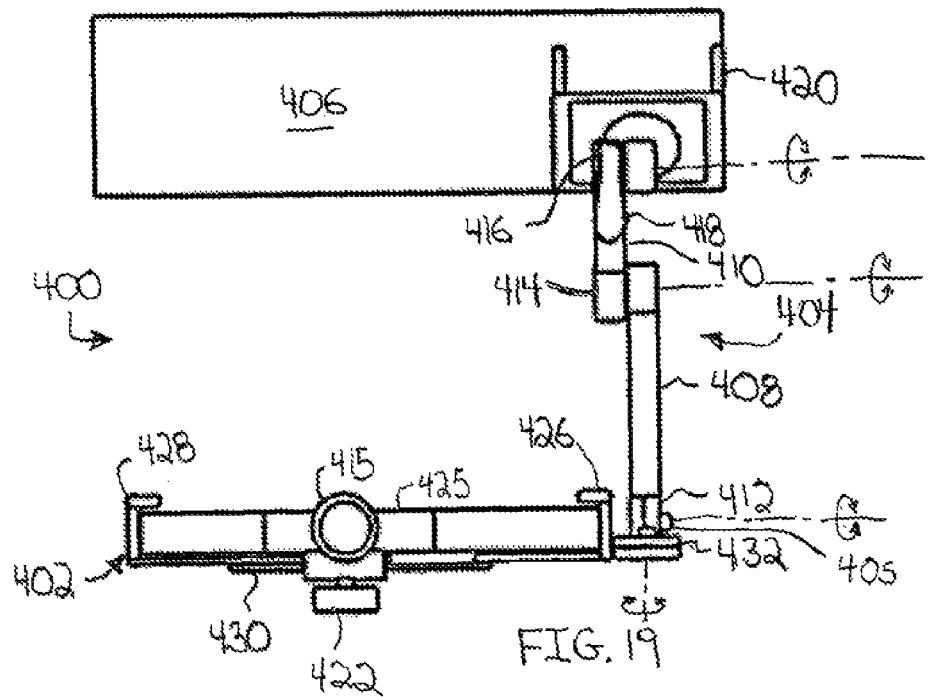
FIG. 19 is a view in front elevation of the support arm attachment for C-arm tables of FIG. 18.
Figure 20:
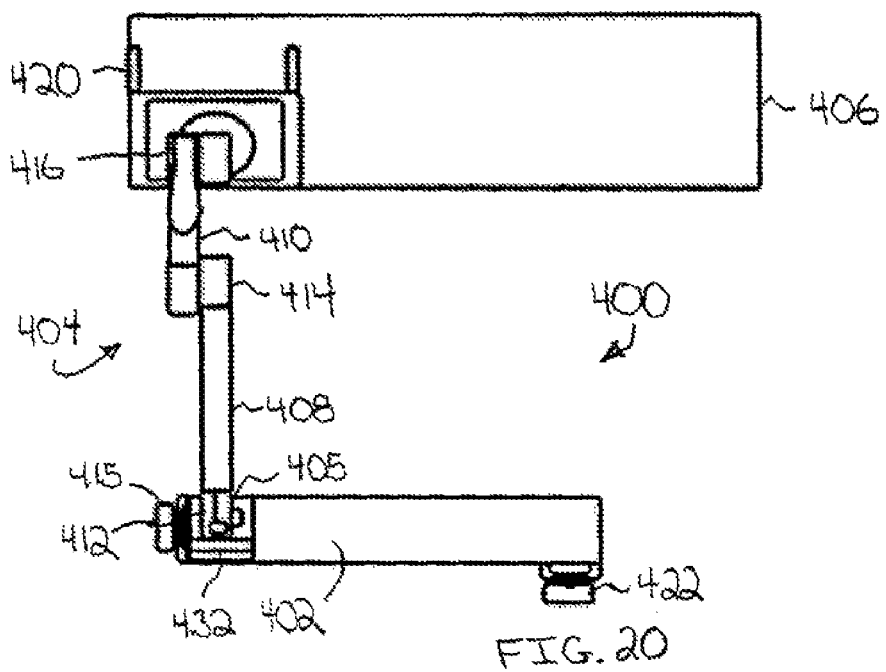
FIG. 20 is a view in side elevation of the support arm attachment for C-arm tables of FIG. 18 with the support arm attachment in an alternative disposition.

The fluoroscopy chairs 10 and 110 disclosed herein achieve a plurality of advantages over the prior art. However, as noted above, there are applications where support will be desired in fluoroscopy procedures where the provision of a dedicated chair 10 or 110 is not practicable, whether based on available space, financial resources, or otherwise. Accordingly, a further alternative of the invention in the form of an adjustable, radio-translucent chest, neck, and head support arm attachment for C-arm tables for radioscopy-guided procedures is depicted in FIGS. 18 through 20 and then in use in FIGS. 21 through 24.

The support arm attachment 400 is founded on a base portion 402 that can be secured to a pre-existing C-arm table 500, preferably by a means for retaining the base portion 402 without mechanical fasteners, such as screws, bolts, or the like. One skilled in the art could conceive of numerous means for accomplishing such a clamping engagement or other engagement without mechanical fasteners communicating between the support arm attachment 400 and the C-arm table 500. In the depicted embodiment, the base portion 402 is retained by clamping means that securely clamp the base portion 402 to the C-arm table 500 as seen in FIGS. 21 through 24. As perhaps best shown in FIG. 19, the clamping means in the present embodiment comprises opposed wall members 426 and 428, each with inwardly turned, overhanging upper panels, that can be selectively drawn into compressive, retaining engagement for a lateral clamping of opposed edges of the platform 502 of the C-arm table 500. Advantageously, in addition to clamping the base portion 402 in place, the relative movement of the opposed wall members 426 and 428 permits the support arm attachment 400 to be adjusted to C-arm tables of varied widths without the use of tools.

In the current embodiment, the opposed wall members 426 and 428 are pulled into compressive engagement by a rack and pinion arrangement 430 that is actuated by a control knob 422. With this, the opposed wall members 426 and 428 can be disposed outboard of opposed edges of the C-arm table 500, and the control knob 422 can be rotated to draw the opposed wall members 426 and 428 together thereby to engage the C-arm table 500 and to restrain the base portion 402 and the support arm attachment 400 in general relative thereto. Additional clamping engagement, in this case vertical clamping from above and below the platform 502 of the C-arm table 500, could be exacted by a control knob 415 that operates a secondary clamping arrangement 425. Under this arrangement, both lateral and vertical clamping could be imparted on the platform 502 of the C-arm table 500 by the lateral clamping provided by the opposed wall members 426 and 428 and the vertical, secondary clamping arrangement 425.

The base portion 402 has one or more receivers 412 disposed thereon for receiving a proximal end of an adjustable support arm 404 either at a fixed angular disposition or at an adjustable angular relationship at a pivot axis 405, which is disposed in a generally horizontal plane. The support arm 404 is articulated. The support arm 404 has a proximal arm member 408 that is pivotally connected to a proximal end of a distal arm member 410 to establish a pivot axis 414. A framework 420 is pivotally coupled to a distal end of the distal arm 420 at a pivot axis 416. The framework 420 retains a chest and neck support member 406. In this embodiment, the support arm 404 is retained outboard of the wall member 426 by the receiver 412, and the chest and neck support member 406 has a body portion that extends inboard toward the opposed wall member 428 and thus over the base portion 402, the clamping arrangement, and the C-arm table 500 in general.

At least the body portion of the chest and neck support member 406 that overlies the C-arm table 500 is radio-translucent. As discussed above, this could be accomplished by forming the chest and neck support member 406 with a core or an entire body portion of a carbon fiber composite or other radio-translucent material. With this, unobstructed fluoroscopic viewing can be achieved while adjustable support is provided to a patient 200. It will be appreciated that the support arm 404 and even the framework 420 may not need to be radio-translucent and could be formed from metal or a similarly structurally sound material.

Each pivoting axis 405, 414, and 416 can be locked at a desired angular disposition by any effective means. In the embodiment depicted herein, a universal locking mechanism is provided in the form of a locking lever 418. Under this arrangement, the pivoting axes 405, 414, and 416 can be freely pivotable when the locking lever 418 is in a given position, such as by being pivoted away from the distal arm member 410. When the pivoting axes 405, 414, and 416 are freely pivotable, the chest and neck support member 406 can be adjusted in height, angular orientation, and longitudinal or lateral position relative to the C-arm table 500. When a desired height, angular orientation, and longitudinal or lateral position of the support member 406 is achieved, the universal locking lever 418 can be actuated, such as by being pivoted toward the distal arm member 410 to lock the height, angle, and position in place. Of course, individual selective locking means for each of the pivot axes 405, 414, and 416 would be readily possible and are within the scope of the invention except as it may be expressly limited.

Figure 21:
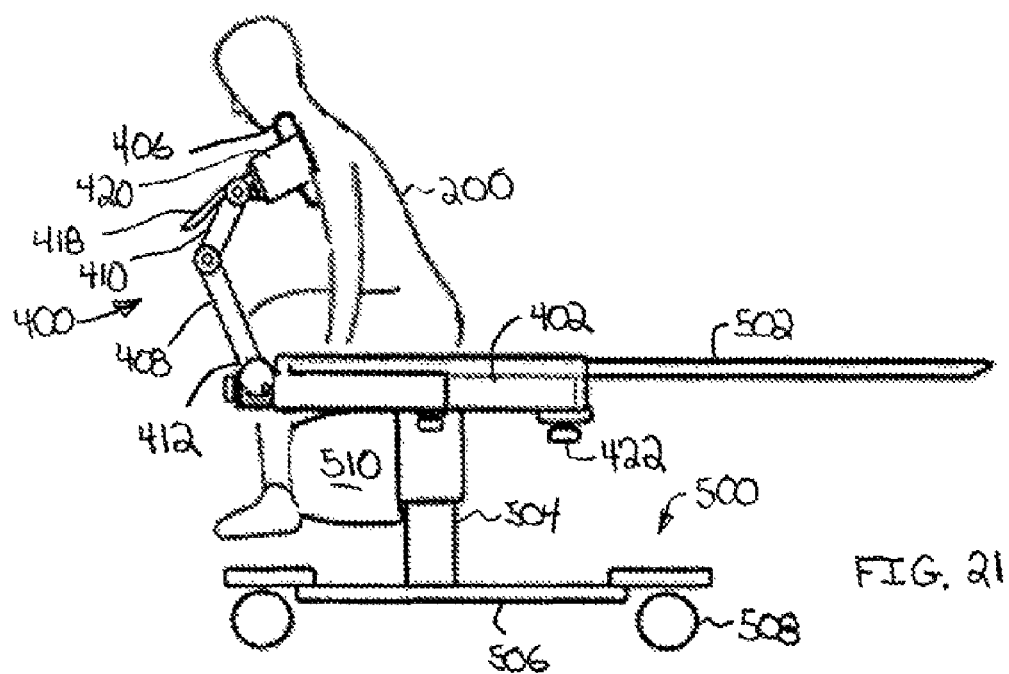
FIGS. 21 and 22 are views in side and front elevation of the support arm attachment attached to a C-arm table with a patient positioned for support.
Figure 22:
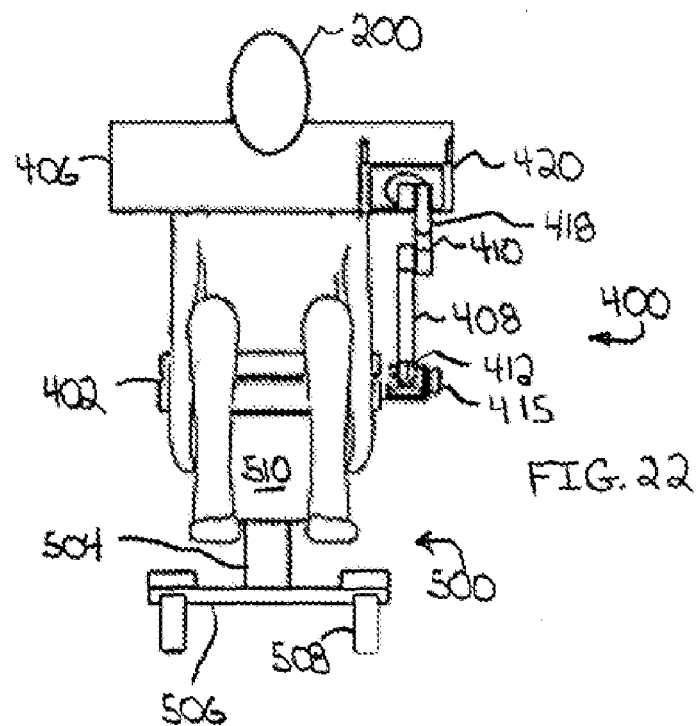

Means can be provided for adjusting the orientation of the support arm 404 relative to the base portion 402 and, consequently, relative to the C-arm table 500. That means could comprise a coupling 432 pivotable about a generally vertical pivot axis between the base of the proximal arm 408 and the base portion 402 whereby the support arm 404 could be pivoted continuously about 360 degrees or some portion or portions thereof. Additionally or alternatively, the proximal end of the proximal arm 408 could be selectively received by the receiver 412 or receivers 412 at different angular orientations. For example, the proximal end of the proximal arm 408 could be received by the receiver 412 in a first angular orientation where the pivot axes 405, 414, and 416 and the support surface presented by the support member 406 are disposed across or lateral to the C-arm table 500 as in FIGS. 21 and 22. With that, a patient 200 can be supported as shown in FIGS. 21 and 22 with his or her body aligned longitudinally with the C-arm table 500 and with the patient's chest supported by the support member 406. With the patient 200 so disposed, his or her feet can be rested against a footrest 510.

Should an emergency arise or should supine, decubitus, or other positioning be required, the patient 200 can simply be repositioned with support being provided by platform 502 of the C-arm table 500. Advantageously, there is no need for repositioning of any elements of the support arm attachment 400 or C-arm table 500 combination; the repositioning can be done immediately without any intermediate steps.

Figure 23:
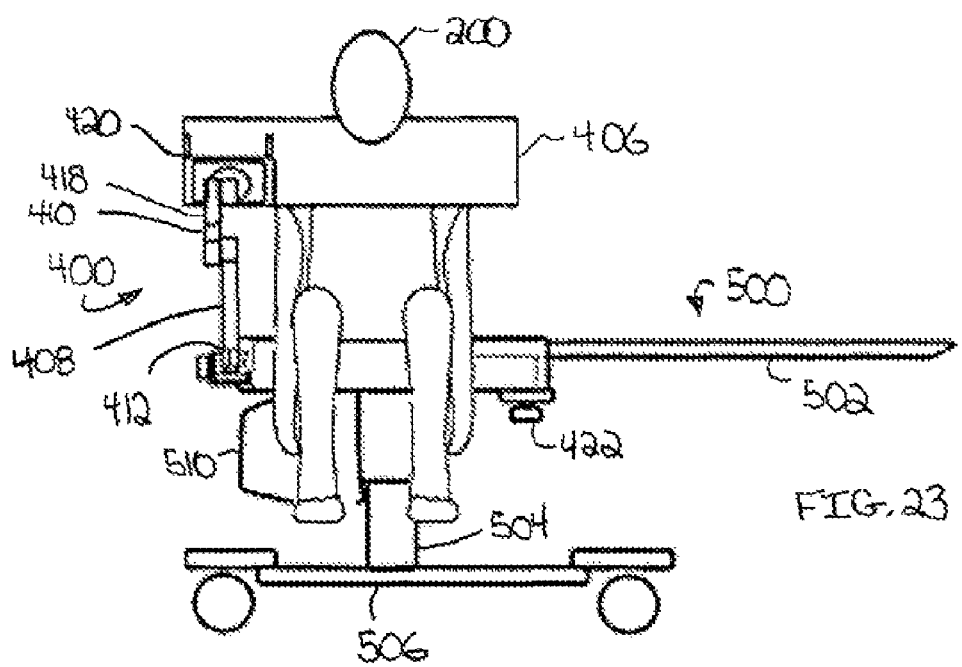
FIGS. 23 and 24 are views in side and front elevation of the support arm arrangement attached in a second orientation relative to the C-arm table, again with a patient positioned for support.
Figure 24:
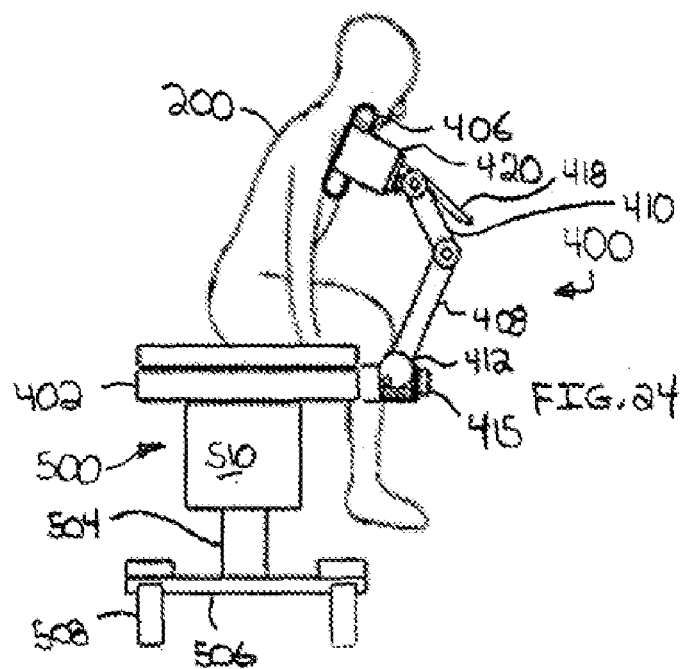

Alternatively, the proximal end of the proximal arm 408 could be received by the receiver 412 in a second angular orientation 90 degrees spaced from the first angular orientation where the pivot axes 405, 414, and 416 and the support surface presented by the support member 406 are disposed in alignment longitudinally with the C-arm table 500 as in FIGS. 23 and 24. Under this configuration, the body of the patient 200 can be disposed orthogonal to the C-arm table 500 as depicted in FIGS. 23 and 24. Additionally, the patient 200 can again be adjusted to a decubitus, supine, or other position requiring support by the platform 502 of the C-arm table 500 without any intermediate steps.

In any case, the height of the patient 200, the platform 502 of the C-arm table 500, and the support arm attachment 400 can be adjusted as necessary for proper fluoroscopic imaging by use of an adjustable support column 504, which can be operated hydraulically, pneumatically, electrically, or by some other mechanism or combination thereof. The base of the support column 504 is retained by a lower platform 506, which in turn is supported by a plurality of selectively lockable wheels 508. By use of the wheels 508, the overall location and orientation of the C-arm table 500, the support arm attachment 400, and a supported patient 200 can be adjusted to facilitate fluoroscopic imaging and other tasks.

Figure 25:
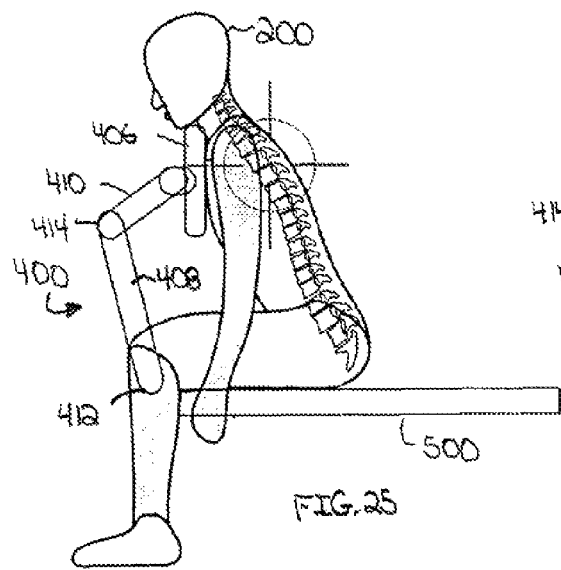
FIGS. 25, 26, and 27 are schematic views in side elevation of the support arm arrangement attached to a C-arm table with a patient supported in varied fluoroscopic viewing positions.
Figure 26:
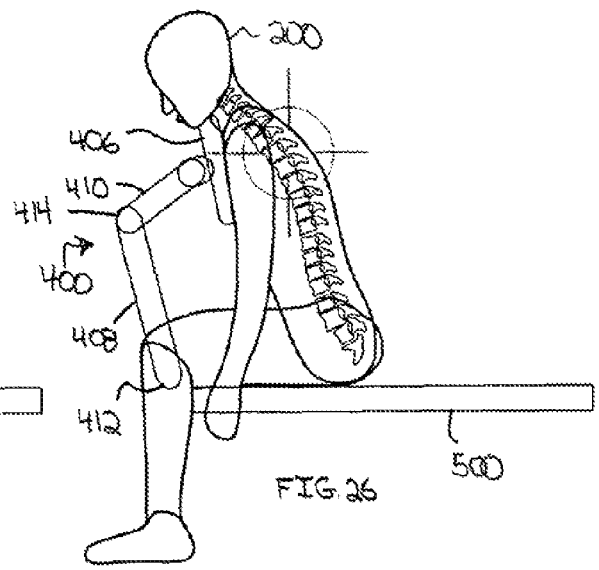
Figure 27:
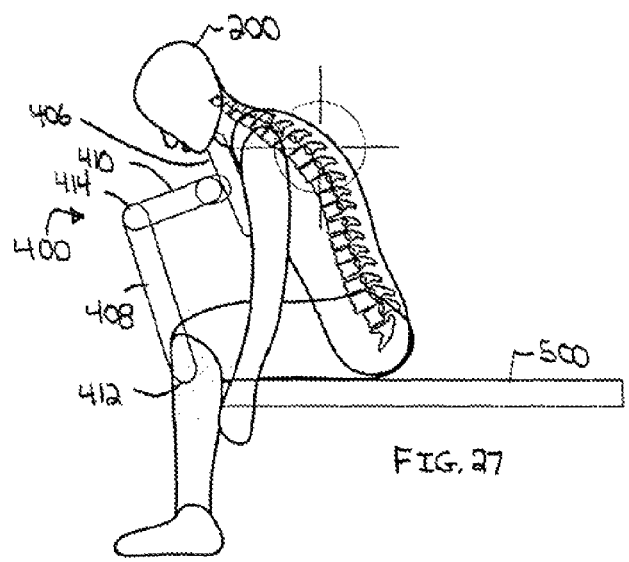

The chest and neck support member 406 can thus be employed to great advantage in fluoroscopic imaging as depicted in FIGS. 25 through 31. As FIGS. 25 through 27 show, the height, longitudinal position, and orientation of the chest and neck support member 406 can be employed to produce varied degrees of expansion and positioning of the epidural spaces in the patient's thoracic region. By a selective positioning of the support member 406, a practitioner can further increase or decrease the expansion of epidural spaces in the patient 200 for easing needle penetration and otherwise facilitating the pain management procedure. In FIG. 27, for example, the support member 406 is rotated away from the patient 200 by a given degree to cause the epidural spaces to be increasingly opened. In FIG. 25, however, the support member 406 is rotated toward the patient 200 in comparison to FIG. 27 whereby the epidural spaces of the patient 200 are only moderately expanded. The positioning of the support member 406 in FIG. 26 can be considered to represent a middle ground of thoracic positioning.

Figure 28:
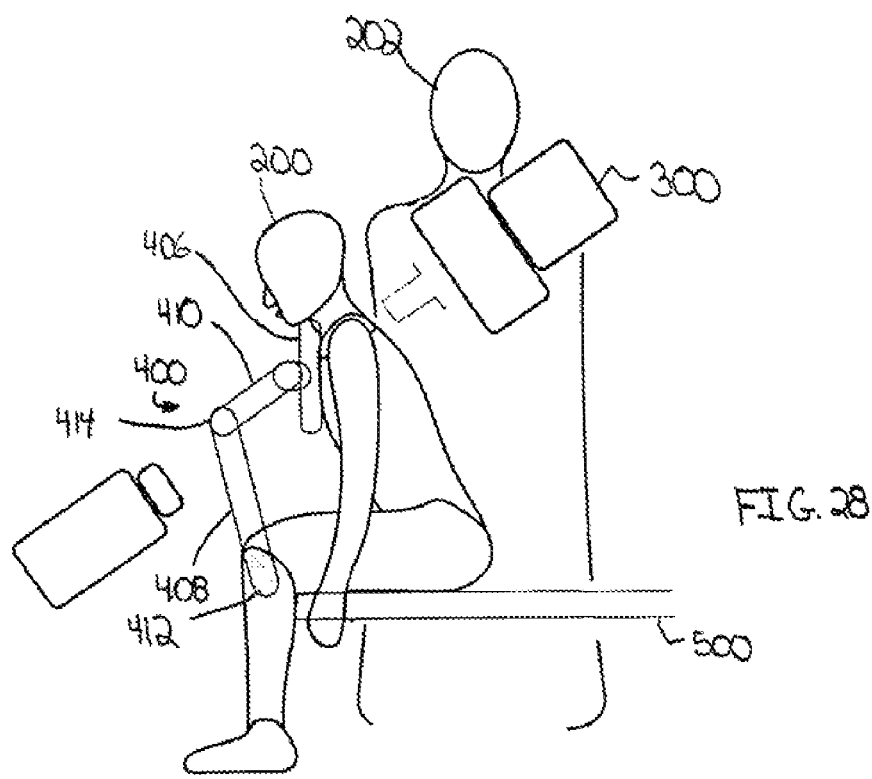
FIGS. 28 and 29 are schematic views in side elevation and top plan of the support arm arrangement retained relative to a C-arm table with a patient supported for anterior-posterior fluoroscopic viewing.
Figure 29:
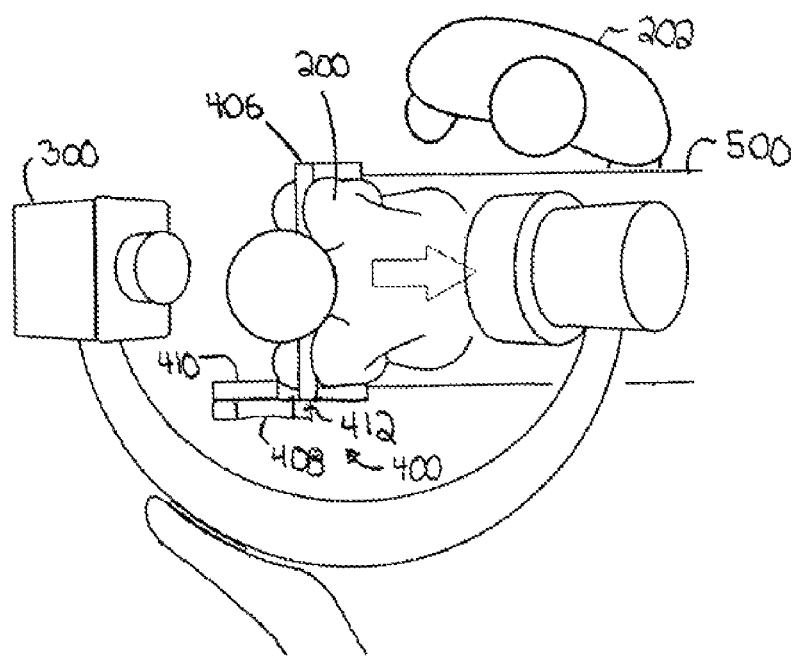
Figure 30:
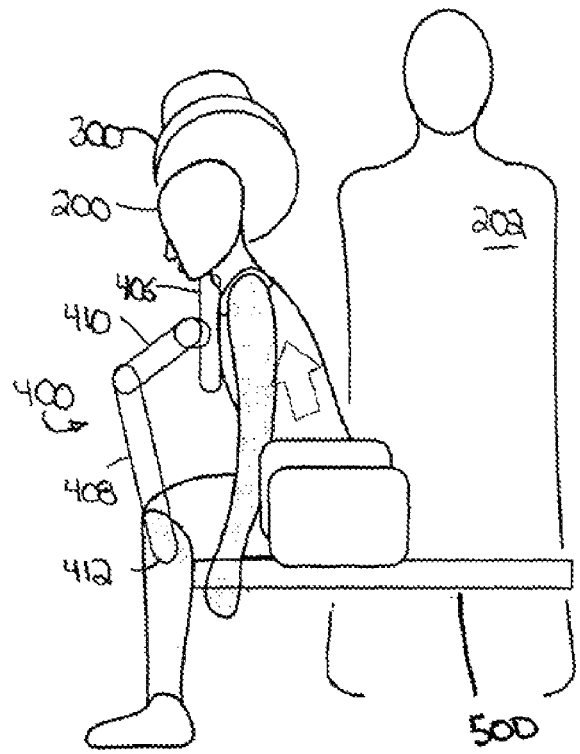
FIGS. 30 and 31 are schematic views in side elevation and top plan of the support arm arrangement alternatively retained relative to a C-arm table with a patient supported for lateral fluoroscopic viewing.
Figure 31:
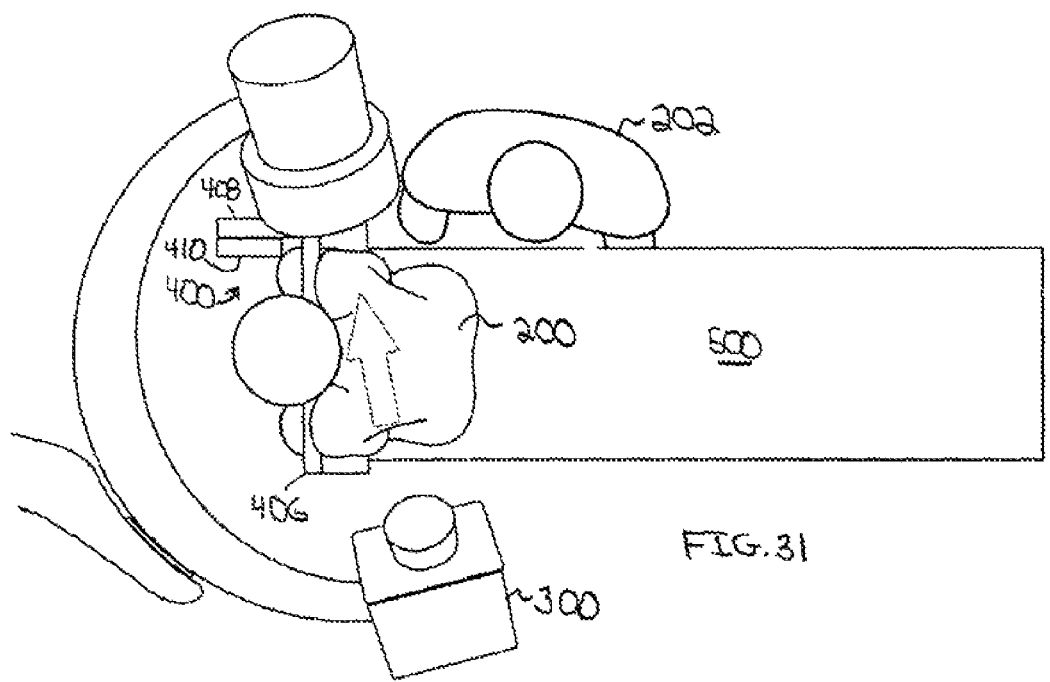

As depicted in FIGS. 28 and 29, the support arm attachment 400 can be employed conveniently to perform anterior-posterior fluoroscopic viewing with the chest hand head of the patient 200 being comfortably supported. Advantageously, with no repositioning of the patient 200 in relation to the C-arm table 500 lateral fluoroscopic viewing can be readily obtained.

It will thus be appreciated that the support arm attachment 400 can be selectively retained relative to a pre-existing C-arm table 500 without the use of mechanical fasteners therebetween to provide fully adjustable, radio-lucent chest, neck, and head support during radioscopy-guided procedures. The support arm attachment 400 thus avoids the need for a dedicated item of equipment by providing added functionality to the pre-existing C-arm table 500. Still further, during periods of non-use, the support arm 404 or the entire support arm attachment 400 can be readily removed or adjusted to permit use of the C-arm table 500 without the support arm attachment 400 and for other purposes.

With certain details of the present inventions for a fluoroscopy chair and support arm attachment for fluoroscopy disclosed, it will be appreciated by one skilled in the art that changes and additions could be made thereto without deviating from the spirit or scope thereof. This is particularly true when one bears in mind that the presently preferred embodiments merely exemplify the broader invention revealed herein. Accordingly, it will be clear that those with certain major features of the claimed invention in mind could craft embodiments that incorporate those major features while not incorporating all of the features included in the preferred embodiments.

Therefore, the following claims are intended to define the scope of protection to be afforded to the inventors. Those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, these claims shall be construed to cover not only the corresponding structure and material expressly described in this specification but also all equivalents thereof that might be now known or hereafter discovered.

We claim as deserving the protection of Letters Patent:

1. A support arm attachment for use during fluoroscopic procedures in relation to a support table with a support platform with opposed lateral edges, the support arm attachment comprising:
   a base portion;
   means for selectively retaining the base portion relative to a platform of a support table;
   a support arm retained by the base portion; and
   a chest and neck support retained by the support arm;
   wherein the means for selectively retaining the base portion relative to a platform of a support table comprises a clamping means whereby the base portion can be retained relative to a platform of a support table without mechanical fasteners between the support arm attachment and a support table, wherein the clamping means comprises a lateral clamping means with means for selectively inducing compressive, retaining engagement of opposed lateral edges of a platform of a support table, and wherein the clamping means comprises first and second opposed wall members for being disposed outboard of opposed lateral edges of a platform of a support table in combination with means for drawing the opposed wall members into compressive engagement with opposed lateral edges of a platform of a support table.

2. The support arm attachment of claim 1 wherein the support arm is retained by the base portion by a receiver wherein the support arm is selectively received by the receiver.

3. The support arm attachment of claim 2 wherein the support arm is adjustable in angular orientation about a vertical axis relative to the base portion.

4. The support arm attachment of claim 3 wherein the support arm is selectively receivable in relation to the receiver in a first angular orientation and a second angular orientation wherein the first angular orientation is spaced 90 degrees from the second angular orientation.

5. The support arm attachment of claim 3 wherein the support arm is pivotable about a vertical axis relative to the base portion.

6. The support arm attachment of claim 1 wherein the support arm is articulated.

7. The support arm attachment of claim 6 wherein the support arm has a proximal arm member that is pivotally connected to a proximal end of a distal arm member to establish a pivot axis and wherein the chest and neck support is pivotable relative to the support arm to establish a pivot axis.

8. The support arm attachment of claim 7 wherein the base portion has opposed wall members, wherein the proximal end of the support arm is retained outboard of the wall members, and wherein the chest and neck support has a body portion that extends inboard toward the opposed wall members and over the base portion.

9. The support arm attachment of claim 6 wherein the chest and neck support is pivotable relative to the support arm.

10. The support arm attachment of claim 1 wherein the support arm is articulated with a proximal arm member pivotally coupled to a distal arm member and the chest and neck support pivotally coupled to the distal arm member.

11. The support arm attachment of claim 10 further comprising means for selectively locking the proximal arm member against pivoting relative to the distal arm member and the chest and neck support against pivoting relative to the distal arm member.

12. The support arm attachment of claim 10 wherein the means for selectively locking the proximal arm member against pivoting relative to the distal arm member and the chest and neck support against pivoting relative to the distal arm member are actuated by a universal locking mechanism comprising a universal locking lever that locks the proximal and distal arm members and the chest and neck support against pivoting.

13. The support arm attachment of claim 1 wherein the means for drawing the opposed wall members into compressive engagement comprises a rack and pinion device in combination with a means for actuating the rack and pinion device.

14. The support arm attachment of claim 1 wherein the clamping means further comprises a vertical clamping means for clamping a platform of a support table from above and below in combination with a means for actuating the vertical clamping means.

15. The support arm attachment of claim 1 wherein the chest and neck support has a body portion comprising a radio-translucent support member.

16. The support arm attachment of claim 1 further comprising a support table with a platform.

17. A support arm attachment for use during fluoroscopic procedures in relation to a support table with a support platform with opposed lateral edges, the support arm attachment comprising:
   a base portion;
   means for selectively retaining the base portion relative to a platform of a support table;
   a support arm retained by the base portion; and
   a chest and neck support retained by the support arm wherein the chest and neck support has a body portion comprising a radio-translucent support member formed form a carbon fiber composite.

* * * * *